United States Patent
Itao

(10) Patent No.: US 11,963,559 B2
(45) Date of Patent: Apr. 23, 2024

(54) ELECTRONIC HEATING/COOLING GARMENT AND ELECTRONIC HEATING/COOLING DEVICE ATTACHABLE TO/DETACHABLE FROM GARMENT

(71) Applicant: WIN HUMAN RECORDER CO., LTD., Tokyo (JP)

(72) Inventor: Kiyoshi Itao, Tokyo (JP)

(73) Assignee: WIN HUMAN RECORDER CO., LTD., Tokyo (JP)

(*) Notice: Subject to any disclaimer, the term of this patent is extended or adjusted under 35 U.S.C. 154(b) by 812 days.

(21) Appl. No.: 16/978,450

(22) PCT Filed: Mar. 1, 2019

(86) PCT No.: PCT/JP2019/008201
§ 371 (c)(1),
(2) Date: Sep. 4, 2020

(87) PCT Pub. No.: WO2019/172143
PCT Pub. Date: Sep. 12, 2019

(65) Prior Publication Data
US 2021/0037900 A1    Feb. 11, 2021

(30) Foreign Application Priority Data

Mar. 5, 2018   (JP) ................................ 2018-039051

(51) Int. Cl.
*A41D 13/00*   (2006.01)
*A41D 13/005*  (2006.01)

(52) U.S. Cl.
CPC ..... *A41D 13/0053* (2013.01); *A41D 13/0051* (2013.01); *A41D 2400/12* (2013.01)

(58) Field of Classification Search
CPC ...... A61F 2007/0011; A61F 2007/0025; A61F 2007/0031; A61F 2007/0054;
(Continued)

(56) References Cited

U.S. PATENT DOCUMENTS 4,962,761 A * 10/1990 Golden ..................... A61F 7/02
                                                    607/104
5,050,604 A *  9/1991 Reshef ................ A61B 5/4266
                                                    600/573
(Continued)

FOREIGN PATENT DOCUMENTS

DE   10 2005 044 402 A1   3/2007
JP       2008-25052 A     2/2008
(Continued)

OTHER PUBLICATIONS

International Search Report dated May 28, 2019 in PCT/JP2019/008201 filed on Mar. 1, 2019, 2 pages.
(Continued)

*Primary Examiner* — Khaled Annis
(74) *Attorney, Agent, or Firm* — Oblon, McClelland, Maier & Neustadt, L.L.P.

(57) ABSTRACT

An electronic heating/cooling garment includes: a neck part, a collar (neckband), or an underarm part where a Peltier device (31) is placed; and a front body or a back body where a heating medium circulation path (35) and a battery (35) are placed, the battery (35) being configured to supply electric power to a pump (341) and the Peltier device (31). The heating medium circulation path (35) is composed of a flexible thermally conductive material having a tubular shape and holds a heating medium therein in an airtight manner. The heating medium circulation path has a first electrode and a second electrode on its outer surface. The first and second electrodes are configured to supply the electric power from the battery (35) to the Peltier device (31) and the pump (341).

4 Claims, 9 Drawing Sheets

(58) Field of Classification Search
CPC ...... A61F 2007/0055; A61F 2007/0056; A61F 2007/0057; A61F 2007/0075; A61F 2007/008; A61F 2007/0086; A61F 2007/0096; A61F 2007/0234; A41D 13/005; A41D 1/002; A41D 13/0025; F25B 21/02

See application file for complete search history.

(56) References Cited

U.S. PATENT DOCUMENTS

| | | | | |
|---|---|---|---|---|
| 9,110,478 | B2* | 8/2015 | Chen | G05D 23/1919 |
| 9,735,893 | B1* | 8/2017 | Aleksov | A61B 5/14532 |
| 2012/0227432 | A1* | 9/2012 | Creech | A41D 13/0053 |
| | | | | 62/259.3 |
| 2013/0238042 | A1* | 9/2013 | Gildersleeve | A61N 1/36021 |
| | | | | 607/104 |
| 2013/0331914 | A1 | 12/2013 | Lee et al. | |
| 2014/0005759 | A1* | 1/2014 | Fahey | A61N 1/0476 |
| | | | | 607/114 |
| 2017/0172227 | A1* | 6/2017 | Fan | A41D 13/0025 |
| 2017/0196731 | A1 | 7/2017 | Debenedictis et al. | |
| 2018/0184901 | A1* | 7/2018 | Akmandor | A61B 5/4848 |
| 2019/0045857 | A1* | 2/2019 | Fan | A41D 13/005 |
| 2019/0099288 | A1 | 4/2019 | Vergara et al. | |
| 2019/0117445 | A1 | 4/2019 | Lee et al. | |
| 2019/0320989 | A1* | 10/2019 | Verma | A61B 6/037 |
| 2020/0100935 | A1 | 4/2020 | Debenedictis et al. | |
| 2021/0037900 | A1* | 2/2021 | Itao | A61F 7/007 |

FOREIGN PATENT DOCUMENTS

| | | |
|---|---|---|
| JP | 2010-70880 A | 4/2010 |
| JP | 2010-82427 A | 4/2010 |
| JP | 2013-248293 A | 12/2013 |
| JP | 2017-110324 A | 6/2017 |
| WO | WO 03/028408 A1 | 4/2003 |
| WO | WO 2017/120538 A1 | 7/2017 |
| WO | WO 2017/172836 A1 | 10/2017 |

OTHER PUBLICATIONS

Yoshida et al., "Shuuchuuryoku wo takametakereba nou wo hiyase! (If You Want to Improve Your Concentration, Cool Your Brain!)", 2011, Wanipurasu, pp. 25-38 (8 total pages) (with partial English translation).

Extended European Search Report dated Mar. 23, 2021 in European Patent Application No. 19763166.6, 12 pages.

* cited by examiner (a1)　　(a2)　　　　(b1)　　(b2)

(a)　　　　　　　　　　　　(b)

ELECTRONIC HEATING/COOLING GARMENT AND ELECTRONIC HEATING/COOLING DEVICE ATTACHABLE TO/DETACHABLE FROM GARMENT

TECHNICAL FIELD

The present invention relates to electronic heating/cooling garments and electronic heating/cooling devices attachable to and detachable from garments.

BACKGROUND ART

Patent Document 1 describes a heating/cooling garment that heats and cools the whole human body with no temperature difference by circulating a heating medium heated and cooled by a Peltier device in a flow path attached to the garment. Patent Document 1 describes that this heating/cooling garment is suitable for wearing in high ambient temperature environments such as steel mills and shipyards or in low ambient temperature environments such as frozen storage warehouses and cold outdoors.

Patent Document 2 describes a body heating/cooling device that heats and cools a human body by directly placing Peltier devices on the carotid body area.

Patent Document 3 describes directly placing Peltier devices on the neck of a human body and controlling the temperature of the Peltier devices based on very low frequency (VLF) components of electrical signals that are generated with heart movement.

Non-Patent Document 1 supervised by the inventor of the present application (hereinafter simply referred to as the inventor) describes principles and applications of wearable air conditioners for cooling the neck. Non-Patent Document 1 describes on pages 27 to 33 that it is most important to keep the temperature of internal tissues such as heart, brain, and intestines, which is called the core body temperature (deep body temperature), constant in order to maintain life activities, and that humans feel "cold and hot" and "comfortable and uncomfortable" in order to appropriately maintain their brain temperature.

CITATION LIST

Patent Documents

PATENT DOCUMENT 1: Japanese Unexamined Patent Publication No. 2008-25052
PATENT DOCUMENT 2: Japanese Unexamined Patent Publication No. 2010-82427
PATENT DOCUMENT 3: Japanese Unexamined Patent Publication No. 2013-248293
Non-Patent Document 1: "Shuuchuuryoku wo takametakereba nou wo hiyase! (If you want to improve your concentration, cool your brain!)," written by Takayoshi Yoshida and WIN Research Group and supervised by Kiyoshi Itao, published by Wanipurasu on Aug. 5, 2011

SUMMARY OF THE INVENTION

Technical Problem

The inventor invented the devices of Patent Document 3 which are configured so that Peltier devices are directly placed on the skin covering large blood vessels running through the neck. The inventor also invented the heating/cooling garment of Patent Document 1 that heats the whole human body with a heating medium and that is used for work in special environments such as hot or cold environments.

Even after that, the inventor continued diligent research and came to the conclusion that there are not only a demand for heating/cooling products having special appearance for work in environments such as hot or cold environments as described in Patent Document 1 but also a potential demand for electronic heating/cooling garments (garments for cooling and/or heating a human body using an electronic device) and electronic heating/cooling devices attachable to and detachable from garments (devices for cooling and/or heating a human body using an electronic device) in a wide range of fields of consumer products that are used by many people.

For example, many people participate in activities such as going out on a hot summer day, watching sports such as baseball or golf or participating in sports (participating in a sports competition) as a hobby, going out on a cold winter day, watching an event held outdoors in a cold area in winter (e.g., New Year's fireworks, a winter sports competition, etc.) or playing winter sports such as skiing and skating as a hobby, and going ice hole fishing for pond smelts. However, the heat or the cold is severe, people are hesitant to participate in such activities as they cannot fully enjoy themselves. This leads to less individuals' social activities and therefore less economic activities, which hinders construction of a more developed society.

One measure to overcome such social problems by technology is to turn the entire space where many people are present into a comfortable environment. However, this requires huge energy consumption and large capital investment and also causes destruction of nature, people's desire for a comfortable environment often conflicts with nature conservation, causing many problems at present. The inventor thought that the best way to eliminate such a conflict is to make electronic heating/cooling garments for individual use popular so that people use them in their daily life.

Since electronic heating/cooling garments does not emit exhaust gas etc., they are highly compatible with nature conservation. Since the total energy consumed by people wearing electronic heating/cooling garments is less than the energy consumption required for heating and cooling the entire environment, the use of the electronic heating/cooling garments will not destroy the natural environment. Moreover, by wearing an electronic heating/cooling garment, the level of heating and cooling can be optimized for each individual. In other words, it is possible to realize a society where conservation of the natural environment and individual comfort are balanced.

The inventor believes that solving the following problems (1) to (3) as viewed from the field of garment products is a prerequisite for solving technical problems. (1) "Providing garments that satisfy individual tastes." When watching events or enjoying sports as a hobby, wearing unique, stylish garments that suit one's own taste is a part of the enjoyment of daily life. (2) "Electronic heating/cooling garments being not easily available in the general market." Unique, stylish electronic heating/cooling garments with electronic heating/cooling functions which suit one's own taste are hard to get unless specially ordered, and neither garment makers nor electronic device manufacturers currently put them on the general market. (3) "Cost reduction of electronic heating/cooling garments." Even if there are companies that provide electronic heating/cooling garments, their price continues to be high under the current circumstances where only individually ordered custom-made products for limited applications can be supplied. If the situation continues to be like this, electronic heating/cooling garments will not become popular. Without solving the above problems (1) to (3) (problems in the field of products), a society where conservation of the natural environment and individual comfort are balanced, which is an ultimate goal, cannot be realized. It is therefore a first technical object to solve the above problems (1) to (3) and widely spread various electronic heating/cooling garments with heating/cooling functions in the society.

The electronic heating/cooling garments can also be regarded as combined products of garments and electronic heating/cooling devices. For garments, some garments are worn for a long period of time, while others are worn only for a short period depending on the trend for each season. On the other hand, expensive electronic devices are typically used over a long period of time, and electronic heating/cooling devices are no exception.

Therefore, even if the first technical object of the present invention is achieved and electronic heating/cooling garments produced as combined products of garments and electronic heating/cooling devices become easily available, there still is the following problem (4) to be solved.

(4) "Difficulty in providing fashionable electronic heating/cooling garments due to the trend-driven nature of fashion." Even if garments that are worn only for a short period of time are combined with electronic heating/cooling devices that can be used for a long period of time, the garments will not be worn when they get out of fashion or when they no longer suit wearer's taste. As a result, there is no longer an opportunity to wear the expensive electronic heating/cooling devices. Fashionable electronic heating/cooling garments are therefore expensive in terms of (price/period of use). As a result, unlike garments for businesses which are needed in many situations, fashionable garments will not create a great demand because they are not essential for general consumers. The fashionable heating/cooling garments therefore continue to be expensive custom-made products and spread slowly.

Once the electronic heating/cooling devices become widespread and are mass-produced and their price is lowered due to the mass production, the electronic heating/cooling devices being discarded after use for a short period of time will not become a big problem in terms of the price, and more and more fashionable electronic heating/cooling garments will be eventually produced. However, it is desired to provide a technique for reusing expensive electronic heating/cooling devices as a technique that helps more quickly spread the electronic heating/cooling garments without just waiting for such time to come. In order to solve the above problem (4), it is a second technical object of the present invention to provide a technique of electronic heating/cooling garments attachable to and detachable from garments, including fashionable garments, that are already available in the market.

The present invention provides an electronic heating/cooling garment that achieves the above first technical object and provides an electronic heating/cooling device attachable to and detachable from a garment which achieves the above second technical object. Main parts of means for solving the problems to achieve the first technical object are the same as those of means for solving the problems to achieve the second technical object. The main parts of the means for solving the problems are means with non-conventional novel features.

Solution to the Problem

An electronic heating/cooling garment according to the invention includes: a neck part, a collar (neckband), or an underarm part where a temperature changing element that can come into contact with skin covering a large blood vessel running through a neck or an armpit is placed; and a front body or a back body where a heating medium circulation path, a pump, and a battery are placed, the heating medium circulation path being thermally coupled to an opposite surface of the temperature changing element from a surface that can come in contact with the skin, the pump being a part of the heating medium circulation path and configured to circulate a heating medium, and the battery being configured to supply electric power to the pump and the temperature changing element. The heating medium circulation path is composed of a flexible, thermally conductive material having a tubular shape, holds the circulating heating medium in a tubular internal space in an airtight manner, and has a first electrode and a second electrode. The first and second electrodes are made of a flexible, electrically conductive material and are configured to supply the electric power from the battery to the temperature changing element and the pump.

An electronic heating/cooling device attachable to or detachable from a garment according to the invention includes: a temperature changing element that can come in contact with skin covering a large blood vessel; a heating medium circulation path thermally coupled to an opposite surface of the temperature changing element from a surface that can come in contact with the skin; a pump that is a part of the heating medium circulation path and is configured to circulate a heating medium; and a battery configured to supply electric power to the pump and the temperature changing element. The heating medium circulation path is composed of a flexible, thermally conductive material having a tubular shape, holds the circulating heating medium in a tubular internal space in an airtight manner, and has a first electrode and a second electrode. The first and second electrodes are made of a flexible, electrically conductive material and are configured to supply the electric power from the battery to the temperature changing element and the pump.

Advantages of the Invention

The electronic heating/cooling garment according to the invention can be easily manufactured by fastening the heating medium circulation path to at least one location in the neck part, the collar (neckband), or the underarm part and the front or back body. Moreover, the temperature changing element is placed in the neck part, the collar (neckband), or the underarm part. Accordingly, the temperature changing element comes in contact with the skin covering the large blood vessel when the electronic heating/cooling garment is worn by a wearer. A deep body temperature can thus be regulated to a proper level.

The electronic heating/cooling device attachable to and detachable from a garment according to the invention can be attached to and detached from various ready-made garments. The temperature changing element comes in contact with the skin covering the large blood vessel when such an electronic heating/cooling garment is worn by a wearer. A deep body temperature can thus be regulated to a proper level.

The electronic heating/cooling garment according to the invention and the electronic heating/cooling device attachable to and detachable from a garment according to the invention do not heat and cool the entire environment, but regulate the deep body temperature to a proper level with the temperature changing element being in contact with the skin covering the large blood vessel. Accordingly, optimal, efficient heating and cooling can be implemented for each individual without destroying nature. Moreover, hypothermia and heatstroke can be prevented if worn all the time. The electronic heating/cooling garment according to the invention and the electronic heating/cooling device attachable to and detachable from a garment according to the invention are thus useful for health management especially for elderly people due to a decline in their ability to regulate the body temperature.

DESCRIPTION OF EMBODIMENTS

Summary of First Embodiment

Figure 1:
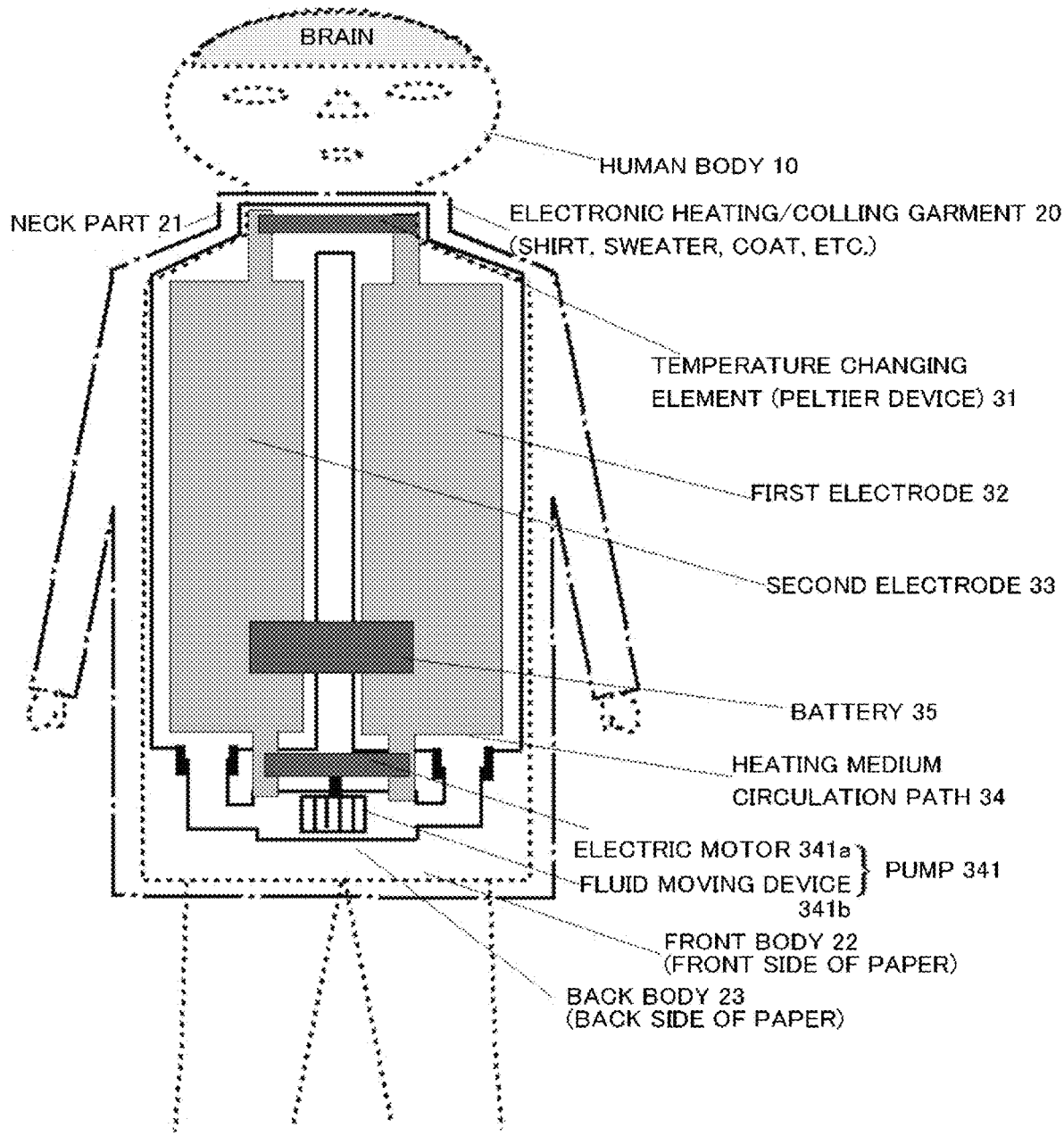
FIG. 1 schematically illustrates an electronic heating/cooling garment according to a first example of a first embodiment.

An electronic heating/cooling garment of the present embodiment includes: a neck part (yoke), a collar (neckband), or an underarm part where a temperature changing element that can come into contact with skin covering a large blood vessel running through a neck or an armpit is placed; and a front body (front panels) or a back body (back panels) where a heating medium circulation path, a pump, and a battery are placed, the heating medium circulation path being thermally coupled to an opposite surface of the temperature changing element from a surface that can come in contact with the skin, the pump being a part of the heating medium circulation path and configured to circulate a heating medium, and the battery being configured to supply electric power to the pump and the temperature changing element.

The heating medium circulation path is composed of a flexible, thermally conductive material (material with flexibility and thermally conductive properties) having a tubular shape, holds the circulating heating medium in a tubular internal space in an airtight manner, and has a first electrode and a second electrode. The first and second electrodes are made of a flexible, electrically conductive material and are configured to supply the electric power from the battery to the temperature changing element and the pump. For the types of garment that do not have a clearly defined neck part, the heating medium circulation path may be fastened to the collar part (collar, neckband) of the garment close to the large blood vessel running through the neck, instead of the neck part. The term "collar" is often used for Western garments, and the term "neckband" is often used for Japanese traditional garments or kimonos.

The above electronic heating/cooling garment of the present embodiment will be briefly described below.

The electronic heating/cooling garment of the present embodiment is a garment for cooling and/or heating a human body using an electronic device. That is, the electronic heating/cooling garment of the present embodiment includes all of a garment for cooling the human body, a garment for heating the human body, and a garment for heating and cooling the human body. A part to be cooled and/or heated is a part of the skin which covers a large blood vessel of the human body.

As described above, large blood vessels running through the neck of the human body run to the brain. Accordingly, with the temperature changing element in contact with the skin covering such a blood vessel, the brain temperature called core body temperature (deep body temperature) can be maintained at a predetermined temperature level, so that the human body can maintain life activities even in hot and cold environments. The feeling of "hot and cold" and "comfortable and uncomfortable" greatly depend on the brain temperature. Therefore, heating and cooling the large blood vessel running through the neck provides much greater comfort than heating and cooling other parts of the human body.

It is troublesome to put the temperature changing element itself directly on the skin covering the large blood vessel running through the neck and it is also troublesome and takes time to take off (remove) the temperature changing element. In the present embodiment, the temperature changing element is therefore placed in the neck part of the garment. The neck part of the garment is the part located closest to the large blood vessel running through the neck among the parts of the garment while the garment is worn. Necklines that directly cover the neck of the human body are often used especially in Western garments. In this case, the temperature changing element can be placed in the neck part of the garment so that the temperature changing element is located closest to the skin covering the large blood vessel running through the neck. Since some kimonos do not have a part corresponding to the clearly defined neck parts of Western garments. In such a case, the temperature changing element is placed in a part of the neckband of the kimono which comes in contact with the skin close to a large blood vessel. The parts of the human body where large blood vessels run near the skin include not only the neck but also the armpit. Accordingly, the temperature changing element may be placed in the underarm part of the garment. Any place close to the skin covering a large blood vessel is an appropriate place for the temperature changing element to contact.

The temperature changing element of the present embodiment is an element to which electric power is supplied to heat a human body or to which electric power is supplied to absorb heat (cool). A Peltier device or a heater that generates heat with a current flowing in a resistor can be used as an element for heating (heating element) for heating garments.

A Peltier device can be used as an element for absorbing heat (heat absorbing element) for cooling garments. A Peltier device can be used as a heating element and a heat absorbing element for heating/cooling garments. The term "temperature changing element" is a superordinate concept of a Peltier device that is a heating/heat absorbing element, and the temperature changing element is an element including various heating elements/heat absorbing elements using a heat pump action, a heater that is a heating element, etc. In the following description of the present embodiment, a Peltier device, which is an embodiment of the temperature changing device, is used as appropriate as a representative example of the temperature changing device.

A Peltier device is an element that functions as both a heating element and a heat absorbing element. From another perspective, one surface of the Peltier device is a heat absorbing surface, and the opposite surface thereof is a heating surface. The heat absorbing surface and the heating surface of the Peltier device are switched according to the current direction in the Peltier device.

The electronic heating/cooling garment of the present embodiment includes the front body or the back body where the heating medium circulation path, the pump, and the battery are placed. The heating medium circulation path is thermally coupled to the opposite surface of the Peltier device from a surface that can come in contact with the skin. The pump is a part of the heating medium circulation path and is configured to circulate a heating medium. The battery is configured to supply electric power to the pump and the Peltier device.

In the electronic heating/cooling garment of the present embodiment, the heating medium circulation path has a tubular shape and functions to circulate the heating medium held in the tubular internal space in an airtight manner. The outer surface of the tubular shape functions to supply the electric power from the battery to the Peltier device and the pump.

Since the heating medium circulation path is made of a flexible, thermally conductive material, the heating medium circulation path deforms according to the shape of the Peltier device, the shape of the human body, the shape of the garment, and the motion of the wearer. By wearing such a heating medium circulation path made of a flexible material together with the garment, the wearer can move freely as desired and does not feel uncomfortable wearing the heating medium circulation path.

First, the function of the heating medium circulation path to circulate the heating medium will be described. This function will be described with respect to the case where the electronic heating/cooling garment functions as an electronic cooling garment and the case where the electronic heating/cooling garment functions as an electronic heating clothes.

When the electronic heating/cooling garment functions as an electronic cooling garment, a current in a predetermined direction is applied to the electrodes of the Peltier device so that the surface of the Peltier device which can come in contact with the skin functions as a heat absorbing surface. At this time, the opposite surface of the Peltier device from the surface that can come in contact with the skin becomes hotter as it functions as a heating surface. In this case, unless the heat in the heating surface is quickly transferred to the outside of the Peltier device, heat transfer occurs between the heat absorbing surface and the heating surface, which causes an increase in temperature of the heat absorbing surface. As a result, the heat absorbing surface no longer performs its expected heat absorbing function.

In order to prevent such a situation, the heating medium circulation path functions to transfer heat released from the heating surface of the Peltier device to the outside of the Peltier device. The heating medium circulation path is thermally coupled to the opposite surface of the Peltier device from the surface that can come in contact with the skin. Accordingly, when the surface of the Peltier device which comes in contact with the skin serves as a heat absorbing surface, the heating surface of the Peltier device is thermally coupled to the heating medium circulation path. Since the heating medium circulation path is made of a material having thermally conductive properties, heat of the heating medium circulating in the heating medium circulation path is transferred to the heating medium circulation path and dissipated to the outside, or heat from the outside of the heating medium circulation path is transferred to the heating medium in the heating medium circulation path.

The heating medium that circulates in the tubular internal space of the heating medium circulation path may be either a gas medium (e.g., air, carbon dioxide, hydrofluorocarbon, etc.) or a liquid medium (e.g., water, coolant mainly composed of ethylene glycol etc. in order to prevent freezing, or oil). The heating medium circulation path has a doughnut shape and is fastened to the neck part, the collar (neckband), or the underarm part, and the front or back body. The pump is placed in the heating medium circulation path. As used herein, the doughnut shape is a doughnut shape in a topological sense. That is, the doughnut shape is not limited to the shape with a circular hole in the center, but include other shapes. The heating medium circulation path may have any shape as long as it functions to circulate the heating medium therein, and the heating medium circulation path may have an uneven surface.

The hotter part of the heating medium gathers in the upper part of the heating medium circulation path. Accordingly, when the wearer is in a standing position, the hotter part of the heating medium stagnates near the heating surface of the Peltier device placed near the neck part, the collar (neckband), or the underarm part of the garment. The pump forces the heating medium to circulate in the heating medium circulation path. As the heating medium is moved, the heat generated in the heating surface flows in the heating medium circulation path extending from near the neck part, the collar (neckband), or the underarm part and along the front part or the back part of the garment, and is dissipated to the outside of the heating medium circulation path and to the outside of the garment while flowing in the heating medium circulation path. Since the heating medium circulation path is composed of the flexible thermally conductive material having a tubular shape, the heating medium circulation path also functions as a heat exchanger (radiator).

The reason why the heating medium circulation path is composed of a flexible, thermally conductive material is that, if the heating medium circulation path is flexible (has the property of being bendable), the wearer cannot move freely with the heating medium circulation path worn on the garment. If the heating medium circulation path is not flexible, the heating medium circulation path may be destroyed due to the external force being concentrated onto a specific point of the heating medium circulation path. If the heating medium circulation path is not thermally conductive (does not have the property of conducting heat), heat cannot be transferred between the heating medium inside the wall of the heating medium circulation path and the outside of the wall of the heating medium circulation path. The heating medium circulation path therefore does not function as a heat exchanger. The amount of heat that is transferred between the inside and outside of the heating medium circulation path depends on the wall thickness of the heating medium circulation path. The heating medium circulation path with a thin wall can function as a heating medium circulation path even if the material of the heating medium circulation path is not so highly thermally conductive.

The heating medium circulation path being composed of a flexible, thermally conductive material having a tubular shape means that the heating medium circulation path may have a portion that is not made of the flexible, thermally conductive material having a tubular shape. Even when the heating medium circulation path has a portion that is not made of the flexible, thermally conductive material having a tubular shape {e.g., a portion made of a flexible, non-thermally conductive material (flexible material and non-thermally conductive material) having a tubular shape, or a portion made of a nonflexible, non-thermally conductive material (nonflexible material and non-thermally conductive material) having a tubular shape}, the proportion of this portion in the heating medium circulation path is low, and depending on where this portion is located in the heating medium circulation path, this portion hardly affects the function of the heating medium circulation path. In the case of using the flexible, non-thermally conductive material, the heating medium circulation path merely has a lower heat exchange function between the heating medium and the external space according to the proportion of the portion made of the flexible, non-thermally conductive material in the heating medium circulation path. In the case of using the nonflexible, non-thermally conductive material, the heating medium circulation path has a lower heat exchange function as in the case of using the flexible, non-thermally conductive material, and the portion made of the nonflexible material merely does not bend. For example, there is a case where a nonflexible, non-thermally conductive material is used as a material of the pump. However, as long as the pump is small, neither the pump hinders wearer's movement nor other people will notice that the pump is there.

Since the heat of the heating medium is dissipated to the outside of the heating medium circulation path, the heating medium will have been cooled by the time it returns to the part of the heating medium circulation path which is thermally coupled to the heating surface of the Peltier device after making one circulation through the heating medium circulation path. The heating medium then takes heat from the heating surface of the Peltier device. The heating medium thus becomes hot again and keeps circulating in the heating medium circulation path. The cooler the heating medium flowing toward the part of the heating medium circulation path which is thermally coupled to the heating surface, the more the heat is transferred from the heating surface to the heating medium, and the less the heat is transferred from the heating surface to the heat absorbing surface of the Peltier device. Heat is therefore transferred from blood vessels under the skin to the heat absorbing surface in an amount larger than that corresponding to the decrease in heat transfer from the heating surface to the heat absorbing surface. Accordingly, more effective cooling is achieved.

The part of the heating medium circulation path which is thermally coupled to the heating surface of the Peltier device is the neck part or collar part of the garment near the large blood vessel running through the neck. It is therefore desirable that the heating medium circulation path extend to a position as far as possible from the heating surface of the Peltier device. In order to prevent the heat of the heating medium in the heating medium circulation path from being transferred back to the human body due to the human body getting too close to the heating medium circulation path, it is desirable that the heat dissipation occur in the lower part of the front or back body of the garment as there is sufficient room between the garment and the human body in the lower part of the front or back body. In the case of using heat dissipation fins that facilitate heat dissipation, it is desirable to place the heat dissipation fins in the lower part of the front or back body.

When the electronic heating/cooling garment functions as an electronic heating garment, a current in the opposite direction to that for heat absorption is applied to the electrodes of the Peltier device so that the surface of the Peltier device which can come in contact with the skin functions as a heating surface. At this time, the opposite surface of the Peltier device from the surface that can come in contact with the skin becomes cooler as it functions as a heat absorbing surface. In this case, unless the cold in the heat absorbing surface is quickly transferred to the outside of the Peltier device (to be more precise, unless the heat of the heating medium in the heating medium circulation path is quickly transferred to the heat absorbing surface of the Peltier device), heat transfer occurs between the heat absorbing surface and the heating surface, which causes a decrease in temperature of the heating surface. As a result, the heating surface no longer performs its expected heating function.

Contrary to the heat transfer from the heating surface to the heating medium circulation path during cooling, heat transfer occurs from the heating medium circulation path to the heat absorbing surface during heating. The thing that is common to cooling and heating is that, in order to enhance the heating/cooling efficiency of the Peltier device, the heating medium circulation path functions to transfer the heat of the heating medium between the opposite surface of the Peltier device from the surface contacting the skin and the heating medium circulation path.

In the case where the electronic heating/cooling garment functions as an electronic heating garment, the heating medium that circulates in the tubular internal space of the heating medium circulation path is the same as that in the case where it functions as an electronic cooling garment. The position of the heating medium circulation path in the garment is also the same as that in the case where the electronic heating/cooling garment functions as an electronic cooling garment. The pump is also placed in the heating medium circuit as in the case where the electronic heating/cooling garment functions as an electronic cooling garment.

The cooler part of the heating medium gathers in the lower part of the heating medium circulation path. Accordingly, when the wearer is in a standing position, the cooler part of the heating medium near the heat absorbing surface of the Peltier device placed near the neck part, the collar (neckband), or the underarm part of the garment flows downward toward the lower parts of the bodies of the garment. Some natural circulation of the heating medium occurs in the heating medium circulation path. However, in order to achieve more satisfactory circulation of the heating medium and to facilitate reliable circulation of the heating medium that does not depend on the body posture, the pump forces the heating medium to circulate in the heat medium circulation path.

The higher the temperature of the heating medium flowing toward the part of the heating medium circulation path which is thermally coupled to the heat absorbing surface, the more the heat is given to the heat absorbing surface, and the higher the heating effect. Accordingly, by placing heat absorption fins on the outer surface of the heating medium circulation path, the heat is more satisfactorily taken, and more effective heating is achieved. The heat dissipation fins for cooling function as the heat absorption fins during heating.

Next, the function of the heating medium circulation path to supply the electric power from the battery to the Peltier device and the pump will be described.

The heating medium circulation path has the first electrode and the second electrode which are made of a flexible, electrically conductive material and are configured to supply the electric power from the battery to the Peltier device and the pump. That is, in addition to the condition of being flexible and the condition of being thermally conductive, namely the condition of being made of a flexible, thermally conductive material as described above, the condition of being electrically conductive is added for the heating medium circulation path of the present embodiment. Only the condition for the electrodes that are new members introduced in terms of power transmission will be described on the assumption that the condition of being flexible and the condition of being thermally conductive are already satisfied.

The first electrode and the second electrode must be structured so that they are electrically insulated from each other. This is because at least a positive (+) electrode and a negative (−) electrode are required to supply electric power to the temperature changing element (Peltier device) and the pump.

The embodiment in which the first and second electrodes electrically insulated from each other are formed on the outer surface of the heating medium circulation path can be implemented by various methods. For example, the heating medium circulation path has a flexible, electrically conductive material portion made of a flexible, electrically conductive material (flexible material and electrically conductive material; e.g., a pipe of copper foil, aluminum foil, etc.) and a flexible, non-electrically conductive material portion made of a flexible, non-electrically conductive material (flexible material and non-electrically conductive material; e.g., a silicone rubber pipe). The first electrode is a first flexible, electrically conductive material portion, and the second electrode is a second flexible, electrically conductive material portion. A first flexible, non-electrically conductive material portion is coupled between one end of the first flexible, electrically conductive material portion and one end of the second flexible, electrically conductive material portion. A second flexible, non-electrically conductive material portion is coupled between the other end of the first flexible, electrically conductive material portion and the other end of the second flexible, electrically conductive material portion. The doughnut-shaped heating medium circulation path from which the heating medium does not leak is thus formed, and the first electrode and the second electrode are electrically insulated from each other by the first flexible, non-electrically conductive material portion and the second flexible, non-electrically conductive material portion (see FIG. 9(b)).

In another embodiment of the first electrode and the second electrode, the heating medium circulation path is made of a flexible, non-electrically conductive material (flexible material and non-electrically conductive material). The first electrode is formed by attaching a first flexible, electrically conductive foil material (flexible, electrically conductive thin foil material: copper foil, aluminum foil, etc.) to the outer surface of the heating medium circulation path, and the second electrode is formed by attaching a second flexible, electrically conductive foil material to the outer surface of the heating medium circulation path (see FIG. 9(a)). This method will be described in more detail in the example described later.

In still another embodiment of the first electrode and the second electrode, the heating medium circulation path is made of a flexible, non-electrically conductive material (flexible material and non-electrically conductive material). The first electrode is a first plated portion (a portion plated with an electrically conductive material) or a first electrically conductive paint portion (a portion coated with an electrically conductive paint) on the outer surface of the heating medium circulation path, and the second electrode is a second plated portion or a second electrically conductive paint portion on the heating medium circulation path (see FIG. 9(c)).

Figure 9:
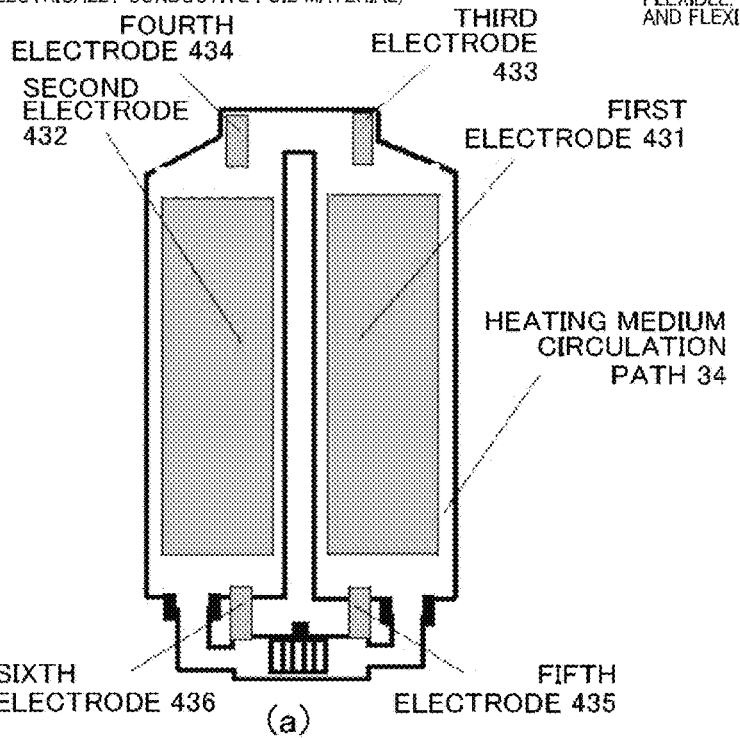
FIG. 9 illustrates various examples of a heating medium circulation path and electrodes of the first and second embodiments.
Figure 9:
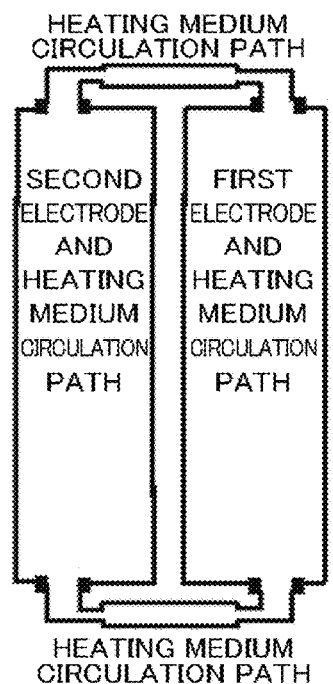
Figure 9:
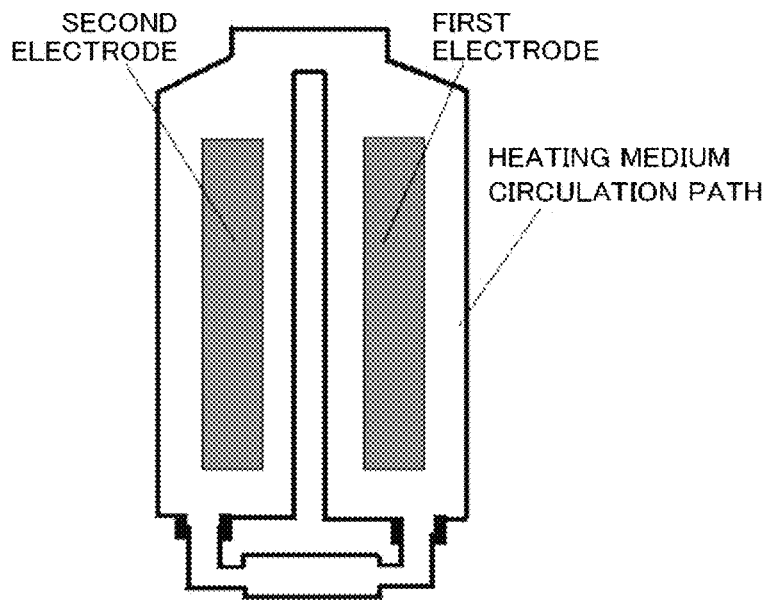

The heating medium circulation paths illustrated in FIGS. 9(a), 9(b), and 9(c) have the following common features. The heating medium circulation path is composed of a flexible, thermally conductive material having a tubular shape, holds the circulating heating medium in the tubular internal space in an airtight manner, and has the first electrode and the second electrode which are made of a flexible, electrically conductive material and are configured to supply the electric power from the battery to the temperature changing element and the pump.

In order for the heating medium circulation path to function as a heat exchanger, it is most desirable that the heating medium circulation paths used in the first embodiment and a second embodiment described later be made of a flexible, thermally conductive material (flexible material and thermally conductive material) having a tubular shape. However, in the case where a part of the heating medium circulation path is made of a flexible non-thermally conductive material (flexible material and non-thermally conductive material), this part made of the flexible, non-thermally conductive material merely does not have a heat exchange function. This is not a serious problem because the remaining part of the heating medium circulation path has a heat exchange function. For example, due to the pump unit's property of being a moving mechanical unit, a part of the heating medium circulation path may be a pump made of a nonflexible, non-thermally conductive material (nonflexible material and non-thermally conductive material).

As a method for fastening the heating medium circulation path to the garment, the heating medium circulation path may be fastened to the neck part, the collar (neckband), or the underarm part, and the front or back part of the garment using thread, or the heating medium circulation path may be fastened to the neck part, the collar (neckband), or the underarm part, and the front or back part of the garment using a hook-and-loop fastener.

Well-known hook-and-loop fasteners consist of the following two parts: "loop" having small loops thereon, and "hook" having small hooks thereon, and the loop and the hook are used in pairs. For example, the hook is attached to the heating medium circulation path, and the loop is attached to the surface of the garment. When the hook and the loop are pressed together, the hooks catch in the loops, and the hook and the loop are fastened together.

For the battery and the pump, the heat absorption fins or the heat dissipation fins can be placed in the lower part of the front or back body which is a part of the garment where there is room between the wearer's body and the garment. For example, the garment may have one or more storage pockets in a relatively low part of the front or back body so that the battery and the pump can be stored therein. The heat dissipation fins thermally coupled to the heating medium circulation path may also be stored in the storage pocket in the relatively low part of the front or back body.

The pump is composed of a sealed casing having a suction port and a discharge port, a fluid moving device (e.g., a piston or a fan) placed in the sealed casing, and an electric motor placed outside the sealed casing in order to drive the fluid moving device. The suction port of the pump is connected to one tubular end of the heating medium circulation path in such a manner that the heating medium does not leak, and the discharge port of the pump is connected to the other tubular end of the heating medium circulation path in such a manner that the heating medium does not leak. The pump functions to circulate the heating medium in the heating medium circulation path and also functions as a part of the doughnut-shaped heating medium circulation path. In this embodiment, the direction in which the heating medium flows in the heating medium circulation path does not affect the functions. Further, each of the suction port and the discharge port can serve as both the suction port and the discharge port depending on the direction of the flow of the heating medium.

Electric power for the electric motor that drives the fluid moving device is supplied from the first and second electrodes that are placed outside the heating medium circulation path. The source of this electric power is the battery, and the electric power generated by the battery is supplied not only to the pump but also to the temperature changing element through the first and second electrodes. By switching the direction of the current that is supplied to the temperature changing element via the first and second electrodes, the heating/cooling garment functions as either a cooling garment or a heating garment.

Summary of Second Embodiment

An electronic heating/cooling device attachable to and detachable from a garment according to the present embodiment includes: a temperature changing element that can come in contact with skin covering a large blood vessel; a heating medium circulation path thermally coupled to an opposite surface of the temperature changing element from a surface that can come in contact with the skin; a pump that is a part of the heating medium circulation path and is configured to circulate a heating medium; and a battery configured to supply electric power to the pump and the temperature changing element.

In the electronic heating/cooling device attachable to and detachable from a garment according to the present embodiment, the heating medium circulation path is composed of a flexible, thermally conductive material having a tubular shape, holds the circulating heating medium in a tubular internal space in an airtight manner, and has a first electrode and a second electrode. The first and second electrodes are made of a flexible, electrically conductive material and are configured to supply the electric power from the battery to the temperature changing element and the pump.

The first and second embodiments have the following novel technical features in common. (1) Both embodiments have the heating medium circulation path thermally coupled to the opposite surface of the temperature changing element from the surface that can come in contact with the skin; the pump that is a part of the heating medium circulation path and is configured to circulate the heating medium; and the battery configured to supply electric power to the pump and the temperature changing element. (2) The heating medium circulation path is composed of a flexible, thermally conductive material having a tubular shape, holds the circulating heating medium in the tubular internal space in an airtight manner, and has the first and second electrodes that are made of a flexible, electrically conductive material and are configured to supply the electric power from the battery to the temperature changing element and the pump.

The substantial difference in configuration between the second embodiment and the first embodiment is that, in the first embodiment, the garment has the electronic heating/cooling device of the second embodiment fastened thereto, whereas in the second embodiment, the electronic heating/cooling device is attachable to and detachable from a garment. Since the main parts of the electronic heating/cooling device attachable to and detachable from a garment according to the second embodiment are the same as those of the electronic heating/cooling garment of the first embodiment, detailed summary of the second embodiment will be omitted.

The embodiments will be described in detail with reference to the accompanying drawings.

First Example of First Embodiment

FIG. 1 schematically illustrates an electronic heating/cooling garment of the first embodiment. An example of the first embodiment will be described with reference to FIG. 1.

FIG. 1 schematically illustrates the relationship between a human body 10 (dashed line in FIG. 1) and an electronic heating/cooling garment 20 (long dashed short dashed line in FIG. 1). The electronic heating/cooling garment 20 is a garment such as a shirt, sweater, or coat with various heating/cooling members arranged thereon. The electronic heating/cooling garment 20 can make all of garments that cover at least the upper body of a human, such as winter coats, raincoats, undershirts, suits, jackets, windbreakers, blazers, work clothes, workwear, and uniforms, function as a heating/cooling garment of the example.

One well-known type of garment is a garment having a front body composed of an upper front body with buttonholes and a lower front body with buttons. This type of garment (first type) can be worn in two ways: worn open without buttoning, and worn with the upper and lower front bodies fastened by buttoning. Another well-known type of garment (second type) is a garment with a zipper front and can be worn in two ways: worn open without zipping, and worn with the right and left front bodies fastened by zipping. For a garment of the first or second type, it is well known to put it on the upper body of a human by opening the two parts of the front body. It is also well known to keep the two parts of the front body fastened after putting the garment on so that the garment properly fits on the upper body of a human.

In the case where the garment of the first or second type is used as the electronic heating/cooling garment 20 shown in FIG. 1, it is difficult to place a heating medium circulation path 34 in a front body 22. In the garments of the first and second type, the front body 22 is composed of two parts. However, it is difficult to divide the heating medium circulation path 34 into two parts as it is a closed flow path for a heating medium. Accordingly, in the case where the garment of the first or second type is used as the electronic heating/cooling garment 20 shown in FIG. 1, the heating medium circulation path 34 is placed in a back body 23.

Still another well-known type of garment (third type) is a garment that is put on by pulling it over the head and taken off by pulling it off over the head. In the case where a garment of the third type is used as the electronic heating/cooling garment 20 shown in FIG. 1, it is possible to place the heating medium circulation path 34 in both of the front body 22 and the back body 23. In the garment of the third type, it is also possible to place the heating medium circulation path 34 in regions extending between the front body 22 and the back body 23.

A further well-known type of garment (fourth type) is an athletic garment with a zipper back, whose front body has a flat surface with no buttons or zipper. Other well-known garments that are put on by opening and closing the back like the athletic garments are dresses that are formal wear worn by women at formal parties. In the case where a garment of the fourth type that is put on by opening and closing the back is used as the electronic heating/cooling garment 20, it is possible to place the heating medium circulation path 34 in the front body 22.

In the present embodiment, a Peltier device 31, which is an embodiment of the temperature changing element, is placed around a neck part (including a collar and a neckband) of the garment. There are various types of neckline. A neckline called high neck rises high along the neck continuously from the bodies of a garment with no fold. A garment with a neckline called turtleneck is worn with the neck part folded down. A neckline called mock turtleneck rises lower than the high neck and covers only the lower part of the neck of a human body.

In the present embodiment, the high neck, the turtleneck, and the mock turtleneck are the suitable places to attaching the Peltier device 31. For example, as shown in FIG. 1 of Patent Document 3 (Japanese Unexamined Patent Publication No. 2013-248293) cited above, attaching the Peltier device 31 to any of these parts has the following advantages over attaching a Peltier device directly to the neck of a human body. The Peltier device attached directly to the neck of a human body makes a garment less fashionable and also makes it difficult to put on and take off the garment. However, by placing the Peltier device 31 around a neck part 21 such as a high neck, turtleneck, or mock turtleneck of the electronic heating/cooling garment 20 of the present embodiment shown in FIG. 1 such that the Peltier device 31 is in contact with the heating medium circulation path 34, the function of the Peltier device 31 is maximized. In addition, the Peltier device 31 placed in the neck part 21 does not make the garment itself less fashionable. Moreover, since the electronic heating/cooling garment 20 can be put on and taken off in a manner similar to that of normal garments, there is no feeling of wearing an electronic device.

Patent Document 2 (Japanese Unexamined Patent Publication No. 2010-82427) cited above describes attaching a Peltier device directly to a human body. Patent Document 2 also describes that "it is said that, on the back of the neck of a human body, there is a switch for arteriovenous anastomoses (AVAs) that regulate body temperature. Heating and cooling the back of the neck opens or closes the AVAs, which makes the heating and cooling more effective due to blood circulation." By placing the Peltier device 31 around the neck part 21 such as the high neck, turtleneck, or mock turtleneck of the electronic heating/cooling garment 20 of the present embodiment such that the Peltier device 31 is located on the heating medium circulation path 34, the effect described in Patent Document 2 is obtained as the Peltier device 31 is also in contact with the "back of the neck."

A kimono has a front body composed of right and left parts that can be opened, and a part of a neckband of the kimono comes in contact with the back of the neck of a human body. Accordingly, in the case where the heating/cooling garment 20 of the present embodiment is a kimono, the part of the neckband which comes in contact with the back of the neck is the optimal place to attach the Peltier device 31.

Wearing a kimono with its neckband set back from the neck of a wearer's body so that the neckband is not in contact with the back of the neck is one well-known way for women to wear a kimono. In this case, not a part of the neckband which corresponds to the back of the neck but a part of the neckband which comes in contact with the skin located as close as possible to a large blood vessel running through the neck is the suitable place to attaching the Peltier device 31.

As described above, the electronic heating/cooling garment 20 composed of a combination of a garment and components related to heating and cooling is applicable to a very wide range of well-known garments. Instead of directly attaching the Peltier device 31 to a human body as described in Patent Documents 2 and 3, the present example uses a configuration in which the Peltier device 31 is attached to a garment and the Peltier device 31 together with the garment comes in contact with the human body 10. It is therefore also possible to place at a desired position a member coupled to the garment and attach the Peltier device 31 to this member so that the Peltier device 31 comes in contact with a desired part of the human body 10. For example, although not shown in FIG. 1, it is also possible to attach the Peltier device 31 so that the Peltier device 31 comes in contact with the armpit where blood vessels circulating blood throughout the body run near the skin.

Moreover, it is possible to place a soft, thermally conductive cushion, hidden by the garment, between the human body 10 and the Peltier device 31. This reduces or eliminates the burden on the human body (discomfort, skin rash). Since a large part of the human body 10 can be supported and covered with the garment, the weight of the members related to heating and cooling is not carried by the neck alone, but can be distributed to the shoulders and other parts of the human body. The weight burden is thus reduced. Moreover, each member related to heating and cooling is covered with a member of the garment or is made to blend into the garment so that the members related to heating and closing do not stand out. Accordingly, the wearer wearing such a foreign object does not stand out as illustrated in the figures of Patent Documents 1 to 3. The wearer therefore no longer needs to worry about looking odd and being stared by others.

FIG. 1 illustrates the case where the Peltier device 31 is attached around the neck part or the collar (neckband). The Peltier device 31 can be similarly attached to an underarm part of the garment by placing the Peltier device in the underarm part of the garment.

Functions of the heating medium circulation path 34 for circulating the heating medium will be described with reference to FIG. 1. When the electronic heating/cooling garment 20 functions as an electronic cooling garment, a current in a predetermined direction is applied to the Peltier device 31 so that the surface of the Peltier device 31 which can come in contact with the skin absorbs heat. For example, a positive electrode of a battery 35 is connected to a first electrode 32 and a negative electrode of the battery 35 is connected to a second electrode 33 so that the surface of the Peltier device 31 which can come in contact with the skin absorbs heat. That is, the surface of the Peltier device 31 which can come in contact with the skin functions as a heat absorbing surface.

The opposite surface of the Peltier device 31 from the surface that can come in contact with the skin is thermally coupled to the heating medium circulation path 34. That is, the heating medium circulation path 34 has a heat rejection function to restrain heat generated by a heating surface of the Peltier device 31 from being transferred to the heat absorbing surface of the Peltier device 31 which can come in contact with the skin. In order to achieve more effective heat rejection, the heat generated by the heating surface of the Peltier device 31 must be efficiently transferred to the heating medium circulation path 34 rather than being transferred to the heat absorbing surface of the Peltier device 31. Heat diffuses from a high temperature area to a low temperature area. Accordingly, the larger the temperature difference between the heating surface (high temperature area) of the Peltier device 31 and a part (low temperature area) of the heating medium circulation path 34 which is thermally coupled to the heating surface of the Peltier device 31 is, the more the heat from the heating surface of the Peltier device 31 is transferred to the heating medium circulation path 34. As a result, the heat rejection function between both surfaces of the Peltier device 31 is enhanced, and the temperature of the heat absorbing surface is kept low. Heat is thus more effectively absorbed from the skin and blood vessels.

The function of a pump 341 is to transfer heat quickly and efficiently from the part of the heating medium circulation path 34 which is thermally coupled to the heating surface. The pump 341 is composed of a fluid moving device 341b that transfers the heating medium that is a fluid, and an electric motor 341a that drives the fluid moving device 341b. The pump 341 shown in FIG. 1 uses a fan as the fluid moving device 341b. The pump 341 rotates the fan by the electric motor 341a to circulate the heating medium in one direction within the heating medium circulation path 34.

The pump 341 forms a part of the heating medium circulation path 34. As shown in FIG. 1, the pump 341 has its one end (e.g., a suction port) inserted in one end of the tubular heating medium circulation path 34 and fixed using an adhesive so that the fluid does not leak. Similarly, the pump 341 has the other end (e.g., a discharge port) inserted in the other end of the tubular heating medium circulation path 34 and fixed using an adhesive so that the fluid does not leak.

Alternatively, although not shown in the figure, the pump 341 may be configured to use a piston with a valve instead of the fan. The pump 341 may reciprocate the piston by the electric motor 341a to circulate the heating medium in one direction within the heating medium circulation path 34 using the valve.

The heating medium heated by the heat generated by the heating surface of the Peltier device 31 dissipates heat while circulating in the heating medium circulation path 34 by the pump. This heating medium therefore will have been cooled by the time it returns to the part of the heating medium circulation path 34 which is thermally coupled to the heating surface of the Peltier device 31. The operation of heating the heating medium by the heat generated by the heating surface of the Peltier device 31 can therefore be repeated. The heat rejection function is thus enhanced, and the temperature of the heat absorbing surface is kept low. As a result, heat is more effectively absorbed from the skin. The heating medium circulation path 34 is made of a flexible, thermally conductive material having a tubular shape. Accordingly, heat is transferred between the heating medium in the heating medium circulation path 34 and the space outside the heating medium circulation path 34 (the environment where the human body is present). The heating medium circulation path 34 thus also functions as a heat exchanger (radiator).

The thickness of the heating medium circulation path 34 is related to the amount of heat that is transferred to the outside space. For example, even in the case where the heating medium circulation path 34 has low thermal conductivity, a large amount of heat is transferred between the heating medium and the outside space when the distance in the direction of heat transfer is short (when the heating medium circulation path 34 is thin). In the case where the heating medium circulation path 34 has high thermal conductivity, the heat of the heating medium diffuses extensively in the heating medium circulation path 34 even when the heating medium circulation path 34 is thick. A large amount of heat is therefore transferred between the heating medium circulation path 34 and the external space. The thickness of the heating medium circulation path 34 (the cross-sectional size of the tubular member) can thus be determined as appropriate according to the thermal conductivity and strength of the material of the heating medium circulation path 34.

In the present embodiment, the heating medium is water, which is a fluid that is easy to handle. In cold areas, coolant is used instead of water to prevent the heating medium from freezing. The direction in which the heating medium circulates in the heating medium circulation path 34 may be clockwise or counterclockwise in FIG. 1. That is, the effect of the heating medium flowing in the heating medium circulation path 34 does not change even when the connection of the battery 35 to the first and second electrodes is reversed. The suction port and the discharge port of the pump 341 are switched when the connection of the battery 35 to the first and second electrodes is reversed.

The heating medium circulation path 34 has on its tubular outer surface the electrically conductive first and second electrodes 32, 33 for transmitting electric power from the battery 35 to the temperature changing element (Peltier device) 31 and the electric motor 341a of the pump 341.

In an example of the first electrode 32 and the second electrode 33, the first electrode 32 and the second electrode 33 are two flexible, electrically conductive thin foil materials (copper foil, aluminum foil, etc.) electrically insulated from each other and attached to the tubular outer surface of the heating medium circulation path 34 made of a flexible, electrically insulating material. In the example, the first electrode 32 and the second electrode 33 are copper foil materials with a thickness of 10 micrometers (μm) to 100 μm attached with an adhesive to the outer surface of the heating medium circulation path 34 made of silicone rubber (see FIG. 9(a)).

Unlike common air conditioners, the heating/cooling garment 20 of the present embodiment has very high heating/cooling efficiency as it directly heats and cools the human body without using air. The total electric power that is transmitted to the Peltier device 31 and the electric motor 341a is about 20 watts (W) during cooling and about 10 W during heating. In the example, the voltage of the battery 35 is 12 volts (V). Accordingly, a current of about 1.7 amperes (A) flows in each of the first and second electrodes 32, 33 during cooling and a current of about 0.85 A flows in each of the first and second electrodes 32, 33 during heating.

When the electronic heating/cooling garment 20 functions as an electronic heating garment, the negative electrode of the battery 35 is connected to the first electrode 32 and the positive electrode of the battery 35 is connected to the second electrode 33 so that the surface of the Peltier device 31 which can come in contact with the skin serves as a heating surface. That is, the surface of the Peltier device 31 which can come in contact with the skin functions as a heating surface. Since the polarities of the battery 35 can be easily switched using a polarity change switch (not shown in FIG. 1), the electronic heating/cooling garment 20 functions as both an electronic heating garment and an electronic cooling garment. When the polarities of the battery 35 are switched using the polarity change switch, the heating medium circulates in the opposite direction in the heating medium circulation path 34. However, as described above, such a change in circulation direction of the heating medium does not affect the heating effect.

It is desirable that heat be exchanged between the heating medium circulation path 34 and the external environment via the outer surface of the garment. For this purpose, only the Peltier device 31 may be attached to the inner surface of the garment, the garment may have a hole extending to the inner and outer surfaces of the garment, and a large part of the heating medium circulation path 34, the battery 35, the pump 341, etc. may be placed outside the garment (see FIG. 7). However, the object of the invention can also be achieved by placing the heating medium circulation path 34 inside the garment (see FIG. 6). The reason why the Peltier device 31 is placed near a large blood vessel running to the brain is to maintain the deep body temperature at a proper temperature level in order to sustain life. Maintaining the deep body temperature at a proper temperature level allows a human to feel comfort. Proper control of the deep body temperature is therefore prioritized, and a slight increase or decrease in temperature of the outer layer of the skin of the human body caused by the heating medium circulation path 34 would not affect so much.

As described above, when the electronic heating/cooling garment 20 functions as an electronic heating garment, the surface of the Peltier device 31 which can come in contact with the skin functions as a heating surface. The opposite surface of the Peltier device 31 from the surface that can come in contact with the skin serves as a heat absorbing surface that absorbs heat from the heating medium circulation path 34. The heat absorbing surface of the Peltier device 31 is thermally coupled to the heating medium circulation path 34 in order to perform heat rejection between the heat absorbing surface and the heating surface of the Peltier device 31 from each other and improve heating efficiency.

Since the heat absorbing surface of the Peltier device 31 is thermally coupled to the heating medium circulation path 34, the heat of the heating medium is transferred to the heat absorbing surface of the Peltier device 31. That is, the heating medium circulation path 34 has a heat rejection function to restrain heat generated by the heat generating surface of the Peltier device 31 which can come in contact with the skin from being transferred to the heat absorbing surface of the Peltier device 31. The heat transfer from the heat generating surface of the Peltier device 31 to the heat absorbing surface of the Peltier device 31 is thus restrained, and the temperature of the heat generating surface of the Peltier device 31 is kept high. The skin and blood vessels are thus heated more effectively.

Second Example of First Embodiment

Figure 2:
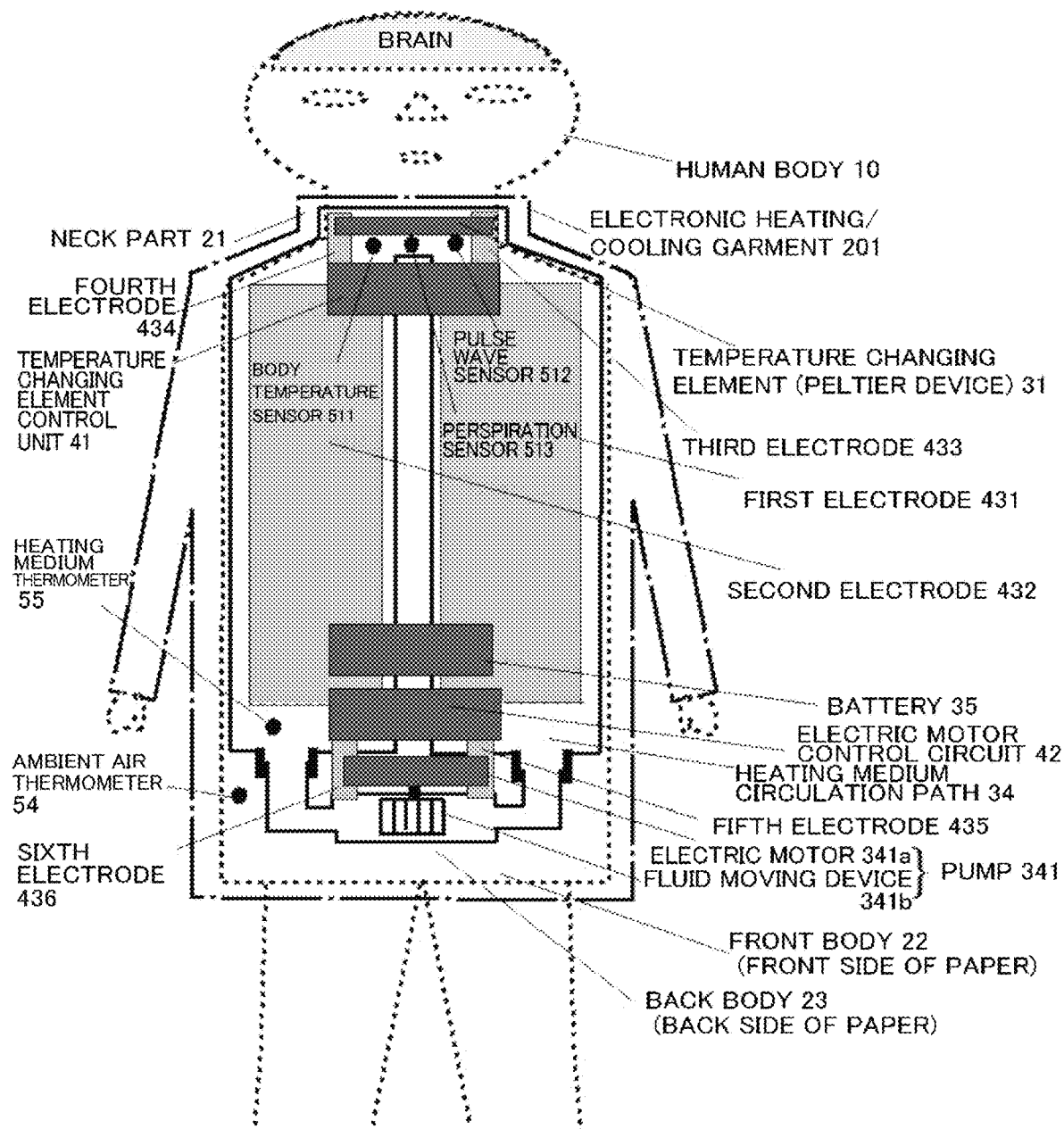
FIG. 2 schematically illustrates an electronic heating/cooling garment according to a second example of the first embodiment.
Figure 3:
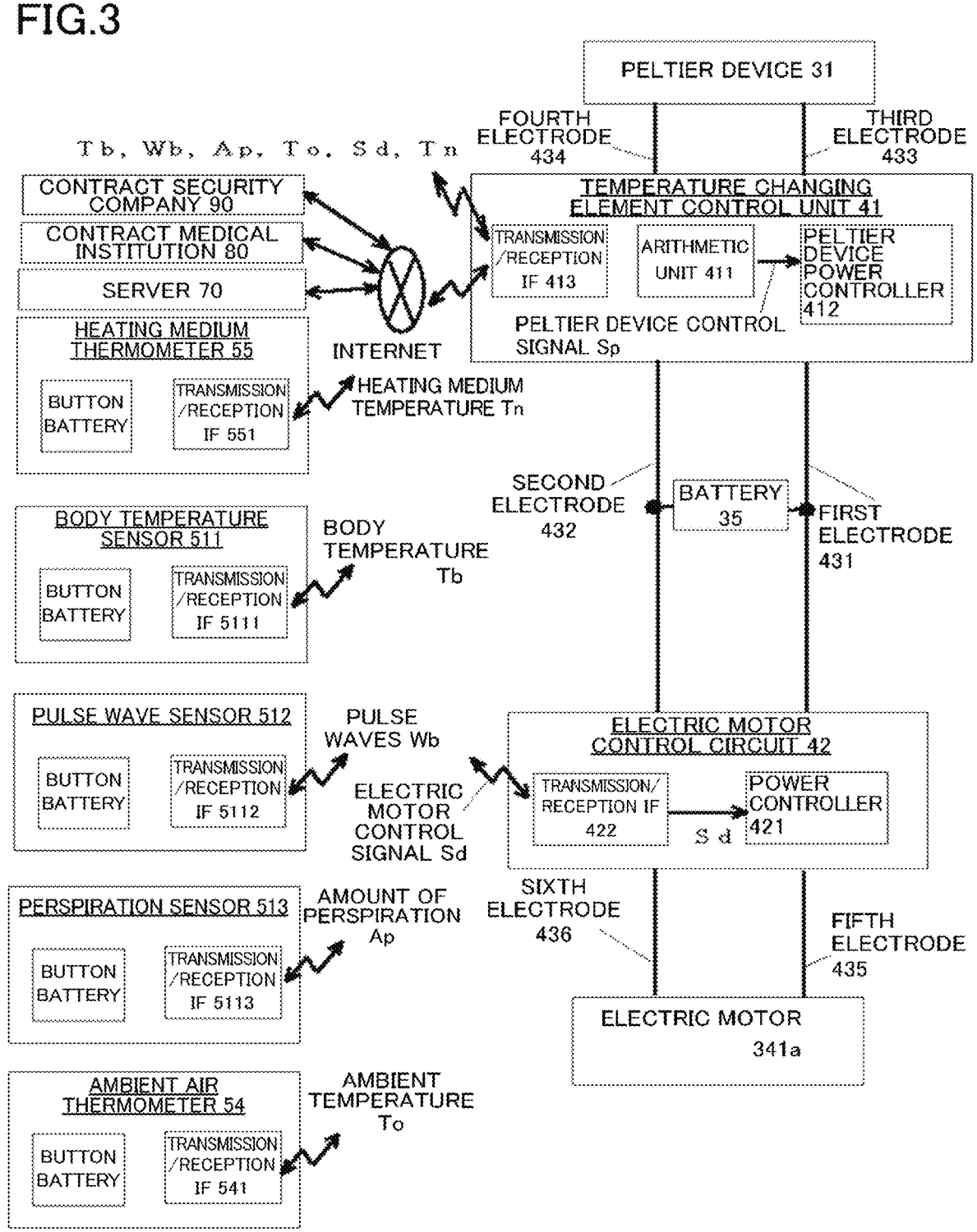
FIG. 3 is a block diagram illustrating the relationship among electronic members placed in the electronic heating/cooling garment of the second example of the first embodiment.

FIG. 2 schematically illustrates an electronic heating/cooling garment 201 of a second example. FIG. 3 is a block diagram illustrating the relationship among electronic members placed in the electronic heating/cooling garment 201. The second example will be described below with reference to FIGS. 2 and 3.

The electronic heating/cooling garment 201 of the second example has various additional components and thus has improved functions as compared to the electronic heating/cooling garment 20 of the first example. The components of the electronic heating/cooling garment 201 which have the same functions and effects as the components of the electronic heating/cooling garment 20 are denoted by the same reference characters, and description thereof will be omitted.

The electronic heating/cooling garment 201 includes a first electrode 431, a third electrode 433, and a fifth electrode 435 which are independent electrodes. The first electrode 431, the third electrode 433, and the fifth electrode 435 are obtained by dividing the first electrode 32 of the first example into three parts. The electronic heating/cooling garment 201 further includes a second electrode 432, a fourth electrode 434, and a sixth electrode 436 which are independent electrodes. The second electrode 432, the fourth electrode 434, and the sixth electrode 436 are obtained by dividing the second electrode 33 of the first example into three parts.

The electronic heating/cooling garment 201 further includes a temperature changing element control unit 41 and an electric motor control circuit 42 which are not included in the electronic heating/cooling garment 20. The temperature changing element control unit 41 is placed between the battery 35 and the temperature changing element (Peltier device) 31. The electric motor control circuit 42 is placed between the battery 35 and the electric motor 341a of the pump 341.

The electronic heating/cooling garment 201 further includes various sensors that are not included in the electronic heating/cooling garment 20, namely a body temperature sensor 511, a pulse wave sensor 512, and a perspiration sensor 513. The body temperature sensor 511 is a well-known sensor called a thermometer that detects a body temperature Tb that is the temperature of the skin surface of the human body. The pulse wave sensor 512 is a well-known sensor that detects pulse waves Wb in blood vessels during blood circulation. The perspiration sensor 513 is a well-known sensor that detects the amount of perspiration Ap that comes out of the skin. The body temperature Tb, the pulse waves Wb, the amount of perspiration Ap, etc. are generally referred to as vital signs. Each sensor contains a micro battery (e.g., a micro button battery for in-the-canal hearing aids) to operate autonomously, and can be fastened to a desired position of the electronic heating/cooling garment 201 using a hook-and-loop fastener, thread, a pocket, or a clip.

The "vital signs" are a medical or healthcare term. The word "vital" means "alive" and the word "sign" means "indication." That is, the vital signs mean signs (life signs) indicating that the human is alive. Examples of the vital signs include the following: the heart is beating, the blood pressure is at least at a certain level, the human is breathing, the human has normal body temperature, the human has urination and bowel movements, the human is responsive, and the brain waves have a specific pattern. The vital signs can be chosen as appropriate according to the object to be achieved.

The pulse waves Wb can also be detected using a well-known electrocardiogram machine. Breathing can be detected using a well-known dynamic air pressure sensor. For urination and bowel movements, the humidity in a diaper after urination or bowel movement can be detected using a well-known humidity detector. Whether being responsive or not can be detected to some extent using a well-known response system composed of a speaker and a microphone. The brain wave pattern can be detected using a well-known electroencephalograph having an electroencephalogram sensor. How to choose the vital signs and how to detect the vital signs are not limited to those described above, and the detecting means is not limited to those described above.

The object to be achieved by the present embodiment is to properly control the deep body temperature in an external environment that is harsh for the human body, and more specifically to maintain a good health condition. It is to prevent hypothermia and heatstroke which are dangerous symptoms especially for elderly people. In view of the object to be solved and the results of research conducted by the inventor, the second example uses the above three types of sensors, which are the body temperature sensor 511, the pulse wave sensor 512, and the perspiration sensor 513, in order to detect the vital sensors. The second example further uses an ambient air thermometer 54 that detects the ambient temperature, which is an external environment sensor, and a heating medium thermometer 55 for controlling heating and cooling. How the Peltier device 31 and the entire system are controlled using these five types of sensors will be described later.

Functions of the temperature changing element control unit 41 and the electric motor control circuit 42 which are the components of the second example not included in the first example will be described below with reference to FIG. 3.

The temperature changing element control unit 41 functions to control the Peltier device 31 that is a temperature changing element. The temperature changing element control unit 41 has an arithmetic unit 411, a Peltier device power controller 412, and a transmission/reception signal interface (transmission/reception IF) 413. The arithmetic unit 411 processes and computes sensor information from each sensor according to a predetermined processing procedure and outputs a Peltier device control signal Sp, which is the computation result, to the Peltier device power controller 412. The Peltier device power controller 412 is a power amplifier that drives the Peltier device 31.

The Peltier device power controller 412 of the temperature changing element control unit 41 will be described first. The electric motor control circuit 42 that drives the electric motor 341*a* of the pump 341, which is also a power amplifier, will then be described. Thereafter, the arithmetic unit 411 of the temperature changing element control unit 41 will be described.

The temperature changing element control unit 41 not only switches the current direction of the Peltier device 31 using the switch as in the first example, but also controls the magnitude of the current that flows in the Peltier device 31 according to the Peltier device control signal Sp that is generated based on the sensor information from the four sensors described above. The Peltier device power controller 412 is therefore composed of power devices (MOSFETs etc.). The Peltier device power controller 412 is a buck DC-to-DC converter that is composed of a well-known full-bridge pulse width modulation (PWM) circuit in order to minimize power loss and reduce size and that generates positive and negative analog voltages. An LC (inductance and capacitance) low pass filter is connected to the output of the buck DC-to-DC converter to convert PWM signals to analog signals. Since all the power control circuits in the second example are of the PWM type, not only power saving and reduction in size but also reduction in thickness of the power control circuits are achieved. The power control circuits therefore do not stick out of the outer or inner surface of the garment so much as to spoil the appearance, and the feeling of discomfort when the garment is worn is minimized.

The first electrode 431 and the second electrode 432, to which the positive and negative electrodes of the battery 35 are connected, are connected to the input of the buck DC-to-DC converter of the Peltier device power controller 412. The output of the low-pass filter of the buck DC-to-DC converter, which is the output of the Peltier device power controller 412, is connected to the third electrode 433 and the fourth electrode 434 to drive the Peltier device 31 connected to the third electrode 433 and the fourth electrode 434.

The electric motor control circuit 42 will be described. In the case where the electric motor 341*a* is an alternating-current (AC) electric motor such as an induction motor, an electric motor power controller 421 of the electric motor control circuit 42 is configured as an inverter composed of a well-known full-bridge PWM circuit. In the case where the electric motor 341*a* is a synchronous motor that is driven by a three-phase alternating current, three electrodes, not shown in FIG. 2, that are extended from the electric motor control circuit 42 are connected to the synchronous motor to drive the synchronous motor.

In the case where the electric motor 341*a* is a direct current (DC) electric motor, the electric motor power controller 421 is a buck DC-to-DC converter or buck-boost DC-to-DC converter that is composed of a well-known full-bridge PWM circuit or a well-known half-bridge PWM circuit. The output of the DC-to-DC converter is connected to the fifth electrode 435 and the sixth electrode 436 to drive the electric motor 341*a* connected to the fifth electrode 435 and the sixth electrode 436. In the second example, it is not necessary to switch the rotational direction of the electric motor 341*a* that is operated by a direct current (DC). It is therefore not necessary to switch the polarity of an electric motor drive voltage that is output from the buck DC-to-DC converter or the buck/boost DC-to-DC converter. The electric motor 341*a* may be an alternating current (AC) electric motor that is driven by an inverter.

The electric motor control circuit 42 includes a transmission/reception signal IF 422 that receives an electric motor control signal Sd sent wirelessly from the temperature changing element control unit 41. The electric motor control circuit 42 can thus receive the electric motor control signal Sd produced by processing and computation in the temperature changing element control unit 41. The electric motor control circuit 42 may processes and computes the sensor information from each sensor to produce the electric motor control signal Sd. However, the above configuration is used in order for the temperature changing element control unit 41 to plays a major role in controlling all the electronic devices of the electronic heating/cooling garment 201 and to ensure consistency in overall operation.

The arithmetic unit 411 of the temperature changing element control unit 41 will be described. The arithmetic unit 411 receives and detects via the transmission/reception signal IF 413 the sensor information sent wirelessly from each sensor. The transmission/reception signal IF 413 functions to send the electric motor control signal Sd for controlling the electric motor control circuit 42 and also functions to connect to the Internet.

Since the sensor information is sent and received wirelessly, where in the garment each sensor is placed is not limited, and an optimal place for collecting desired information can be selected for each sensor. For example, the pulse wave sensor 512 can be placed near a large blood vessel running through the neck, near the heart, between the band of a watch and the skin, etc. The perspiration sensor 513 may be placed near the neck, near a part of the skin which tends to be sweaty, etc. The body temperature sensor 511 may be placed near the neck or near the inside of the armpit. The ambient air thermometer 54 may be placed at a position facing the external environment of the electronic heating/cooling garment 201 and away from the heating medium circulation path 34. It is desirable that the heating medium thermometer 55 be placed near the heating medium circulation path 34.

The arithmetic unit 411 is mainly composed of a micro processing unit (MPU) that is a main component. The arithmetic unit 411 processes and computes the information from the five sensors to produce the Peltier device control signal Sp. The Peltier device control signal Sp is input to the Peltier device power controller 412. The arithmetic unit 411 also processes and computes the information from the five sensors to produce the electric motor control signal Sd. As described above, the electric motor control signal Sd is input to the electric motor power controller 421. For example, when the Peltier device control signal Sp is large, a large amount of heat is transferred between the Peltier device 31 and the heating medium. In this case, the efficiency of the Peltier device 31 is reduced unless the amount of heat transfer per unit time is increased by increasing the flow velocity of the heating medium. Therefore, when the Peltier device control signal Sp is large, reduction in efficiency of the Peltier device 31 is prevented by increasing the electric motor control signal Sd and thus increasing the rotational speed of the electric motor 341a. On the other hand, when the Peltier device control signal Sp is small, unnecessary discharge of the battery 35 is reduced by reducing the electric motor control signal Sd and thus reducing the rotational speed of the electric motor 341a.

In the second example, the heating medium thermometer 55 is placed in close contact with the outer surface of the heating medium circulation path 34. In the case where the thermal conductivity between the heating medium circulation path 34 and the heating medium thermometer 55 is high, the difference between the heating medium temperature Tn that is detected by the heating medium thermometer 55 and the temperature of a thermally conductive medium flowing immediately below the heating medium thermometer 55 is small and the detection accuracy of the heating medium temperature Tn is high. Therefore, the heating medium temperature Tn can be regarded as the temperature of the thermally conductive medium flowing immediately below the heating medium thermometer 55. When the absolute value of the difference between the heating medium temperature Tn and the ambient temperature To is small, it means that the heating medium is functioning satisfactorily. When the absolute value of the difference between the heating medium temperature Tn and the ambient temperature To is large, it means that the heating medium is not functioning well. The rotational speed of the electric motor 341a is thus efficiently controlled by changing the magnitude of the electric motor control signal Sd according to the absolute value of the difference between the heating medium temperature Tn and the ambient temperature To. That is, when the absolute value of the difference between the heating medium temperature Tn and the ambient temperature To is large, the absolute value of the difference between the heating medium temperature Tn and the ambient temperature To is reduced by increasing the rotational speed of the electric motor 341a and thus increasing the flow velocity of the heating medium. The amount of heat transfer by the heating medium is thus increased. On the other hand, when the absolute value of the difference between the heating medium temperature Tn and the ambient temperature To is small, unnecessary power consumption is prevented by reducing the rotational speed of the electric motor 341a.

The processing and computation that are performed by the arithmetic unit 411 of the temperature changing element control unit 41 will be described.

For example, the simplest processing and calculation that are performed by the arithmetic unit 411 is as follows. When the ambient temperature detected by the ambient air thermometer 54 is higher than a predetermined temperature, the arithmetic unit 411 outputs the Peltier device control signal Sp having a constant value that causes the surface of the Peltier device 31 which can come in contact with the skin to serve as a heat absorbing surface. When the ambient temperature detected by the ambient air thermometer 54 is lower than the predetermined temperature, the arithmetic unit 411 outputs the Peltier device control signal Sp having a constant value that causes the surface of the Peltier device 31 which can come in contact with the skin to serve as a heat generating surface. In a modification of this method, the arithmetic unit 411 may output the Peltier device control signal Sp whose absolute value changes according to the difference between the ambient temperature detected by the ambient air thermometer 54 and the predetermined temperature. Such a control law is feedforward control that does not take into consideration at all the effect of the Peltier device 31 on the human body, and therefore the effect of heating and cooling on the human body greatly varies depending on the individual.

One method that eases the disadvantage of the feedforward control is, e.g., feedback control in which the body temperature Tb detected by the body temperature sensor 511 is controlled to a predetermined value. Patent Document 3 (Japanese Unexamined Patent Publication No. 2013-248293) describes that an artificial feedback control system that controls the body temperature Tb to a predetermined value and a feedback control system that controls a biological system in order for the human body to maintain homeostasis, which is the inherent ability of the human body, compete against each other and the body temperature cannot be properly regulated. That is, Patent Document 3 describes that it is not sufficient to perform control using only the body temperature Tb detected on the skin of the body surface which is one of the vital signs.

Accordingly, the electronic heating/cooling garment 201 of the second example uses the following body temperature regulation method using the Peltier device 31 described in Patent Document 3.

The arithmetic unit 411 computes the heart rate per predetermined time from the pulse waves Wb which are time-series information, and computes the frequency components of the heart rate using a well-known fast Fourier transform (FFT). The arithmetic unit 411 detects a value HF related to the activity of the parasympathetic nerves by integrating the components in the frequency band higher than 0.2 Hz, detects a value LF related to the activity of the sympathetic nerves by integrating the components in the frequency band of 0.04 to 0.2 Hz, and detects a value VLF related to the activity of the sympathetic nerves for thermoregulation by integrating the components in the frequency band lower than 0.04 Hz. When the ambient temperature To is higher than a predetermined value, the arithmetic unit 411 determines the polarity of the Peltier device control signal Sp so that the surface of the Peltier device 31 which can come in contact with the skin serves as a heat absorbing surface, and determines the absolute value of the Peltier device control signal Sp according to the value VLF or the amount of perspiration Ap. When the ambient temperature To is lower than the predetermined value, the arithmetic unit 411 determines the polarity of the Peltier device control signal Sp so that the surface of the Peltier device 31 which can come in contact with the skin serves as a heat generating surface, and determines the absolute value of the Peltier device control signal Sp according to the value VLF or the amount of perspiration Ap.

Figure 4:
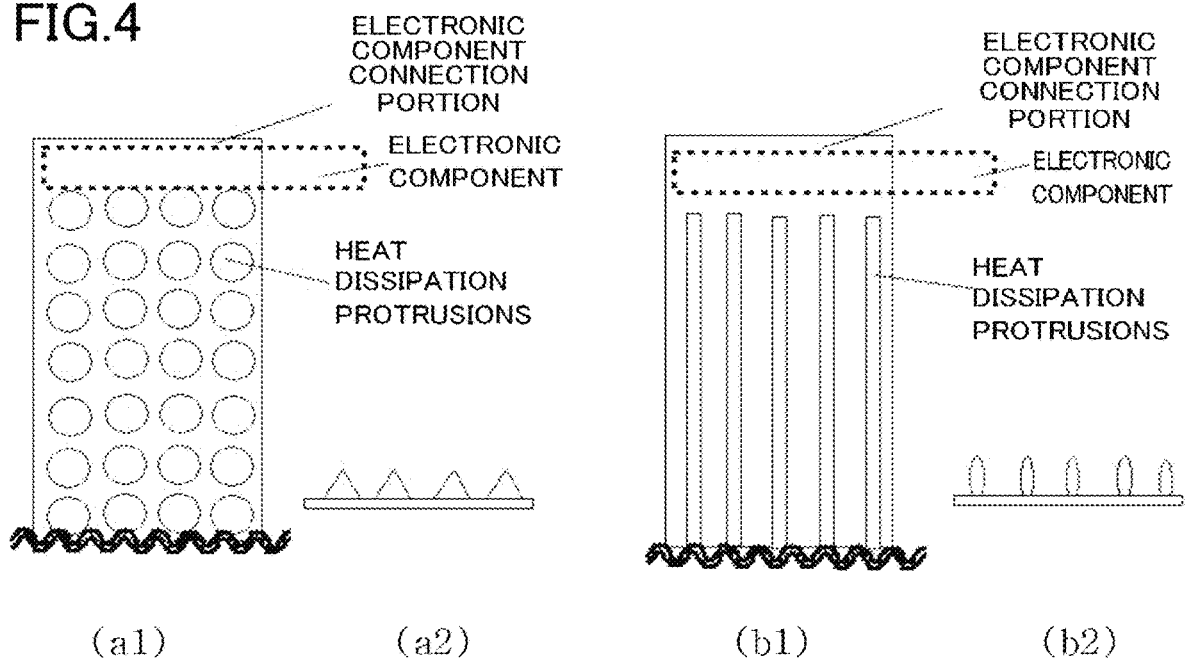
FIG. 4 illustrates a modification of an electrode of the first and second examples of the first embodiment.

FIG. 4 illustrates a modification of the electrode in the first and second examples of the first embodiment. As shown in FIG. 4, the surface area of the thermally conductive electrode placed on the outer surface of the heating medium circulation path 34 may be increased so that the electrode functions as heat absorption fins or heat dissipation fins (hereinafter referred to as the heat absorption/dissipation fins) and dissipates heat more effectively. FIG. 4(a1) is a plan view of the electrode, and FIG. 4(a2) is a sectional view of the electrode. The electrode has conical protrusions on its surface so that an increased surface area of the electrode comes in contact with the outside air. The electrode has no conical protrusion in an area connected to an electronic member (shown by dashed line in FIG. 4) so that the electrode has low contact resistance in this area. FIGS. 4(b1) and 4(b2) illustrate another example of the electrode. FIG. 4(b1) is a plan view of the electrode, and FIG. 4(b2) is a sectional view of the electrode. The electrode has linear protrusions on its surface so that an increased surface area of the electrode comes in contact with the outside air. The electrode has no linear protrusion in an area connected to the electronic member so that the electrode has low contact resistance in this area.

Figure 5:
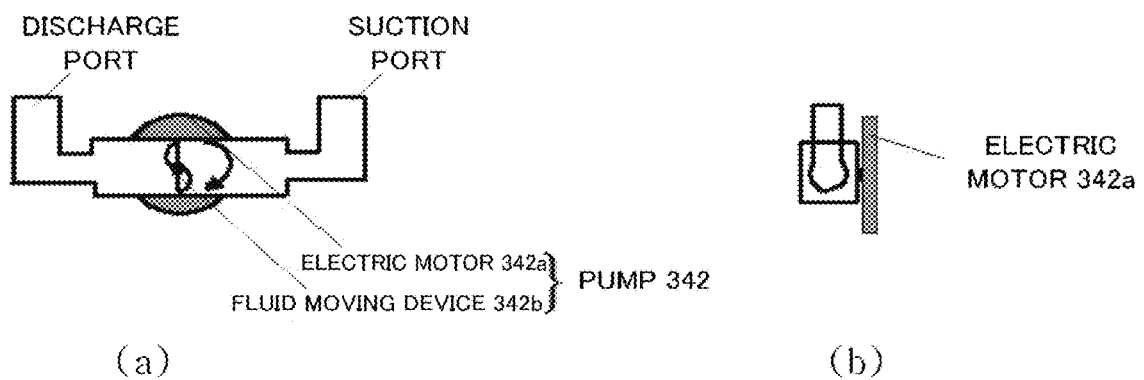
FIG. 5 illustrates a modification of a pump of the first and second examples of the first embodiment.

FIG. 5 illustrates a modification of the pump of the first and second examples of the first embodiment. As shown in FIG. 5, a flat pump 342 may be used which is flat in a direction parallel to the plane of the fabric of the garment. FIG. 5(a) is a plan view and FIG. 5(b) is a side view. The pump 342 uses an electric motor 342a that is flat in the planar direction of the cloth, and a fluid moving device 342b that is flat in the planar direction of the cloth. The flat electric motor 342a may be a well-known brushless synchronous electric motor having flat magnets and flat windings facing the flat magnets. The flat fluid moving device 342b can be formed using a bowl-shaped propeller. When the bowl-shaped propeller is rotated in the direction shown by arrow in FIG. 5(a), the heating medium is moved from the suction port toward the discharge port. By using the pump 342 that is flat in the direction parallel to the plane of the fabric of the garment, the wearer does not feel discomfort, the garment does not become unnaturally uneven, and the wearer does not look odd to other people.

Figure 6:
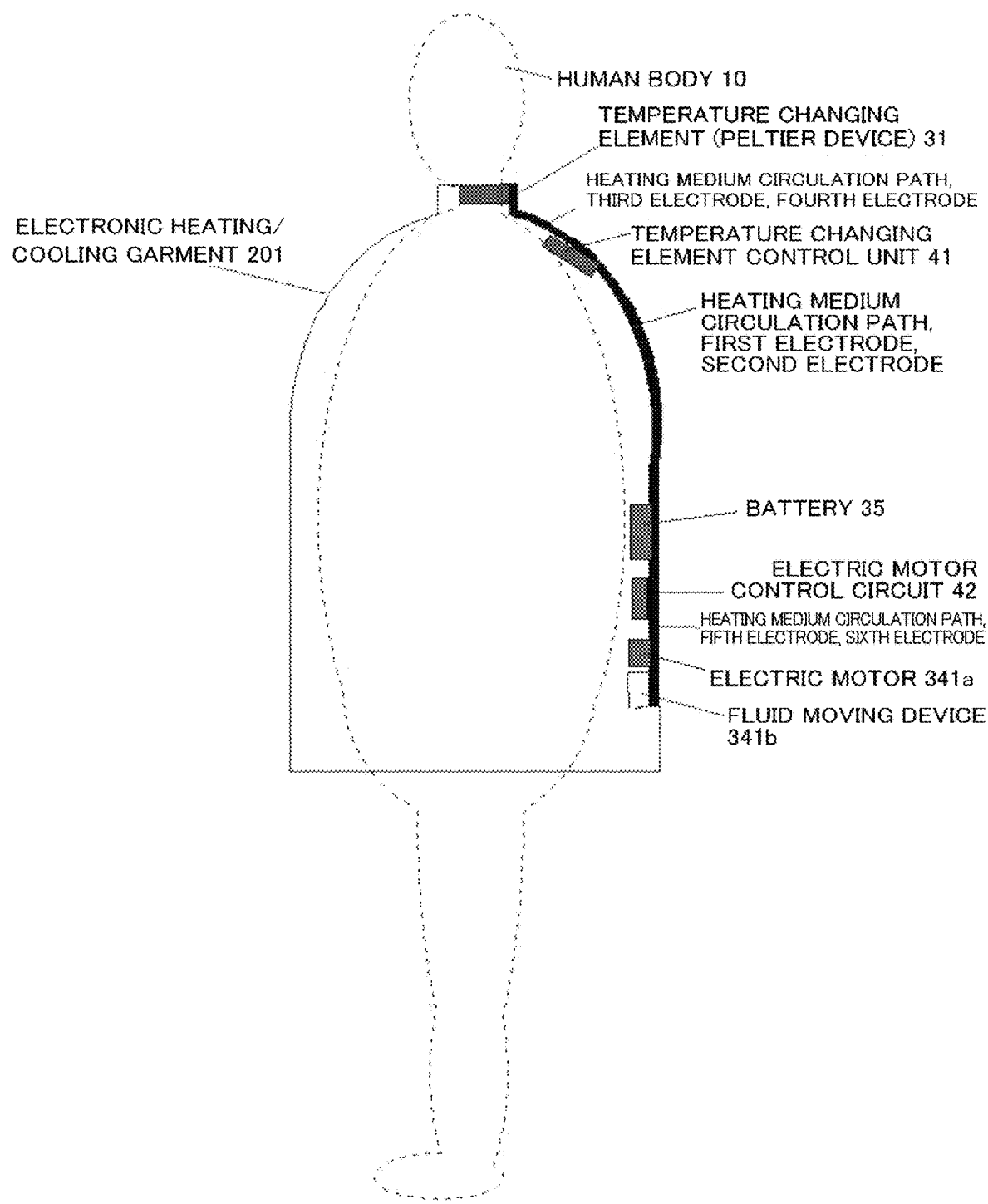
FIG. 6 is a longitudinal section of the electronic heating/cooling garment of the second example of the first embodiment.

FIG. 6 is a longitudinal section of the electronic heating/cooling garment 201 of the second example of the first embodiment. All the electronic members including the heating medium circulation path 34 are placed inside the electronic heating/cooling garment 201. Accordingly, heat is transferred between the heating medium circulation path 34 and the inside of the electronic heating/cooling garment 201, and this heat transfer affects the internal temperature of the electronic heating/cooling garment 201. However, as described above, a slight uniform increase or decrease in internal temperature is allowable as the benefit obtained by properly regulating the deep body temperature by the Peltier device 31 is greater than the disadvantage caused by such an increase or decrease in internal temperature.

Figure 7:
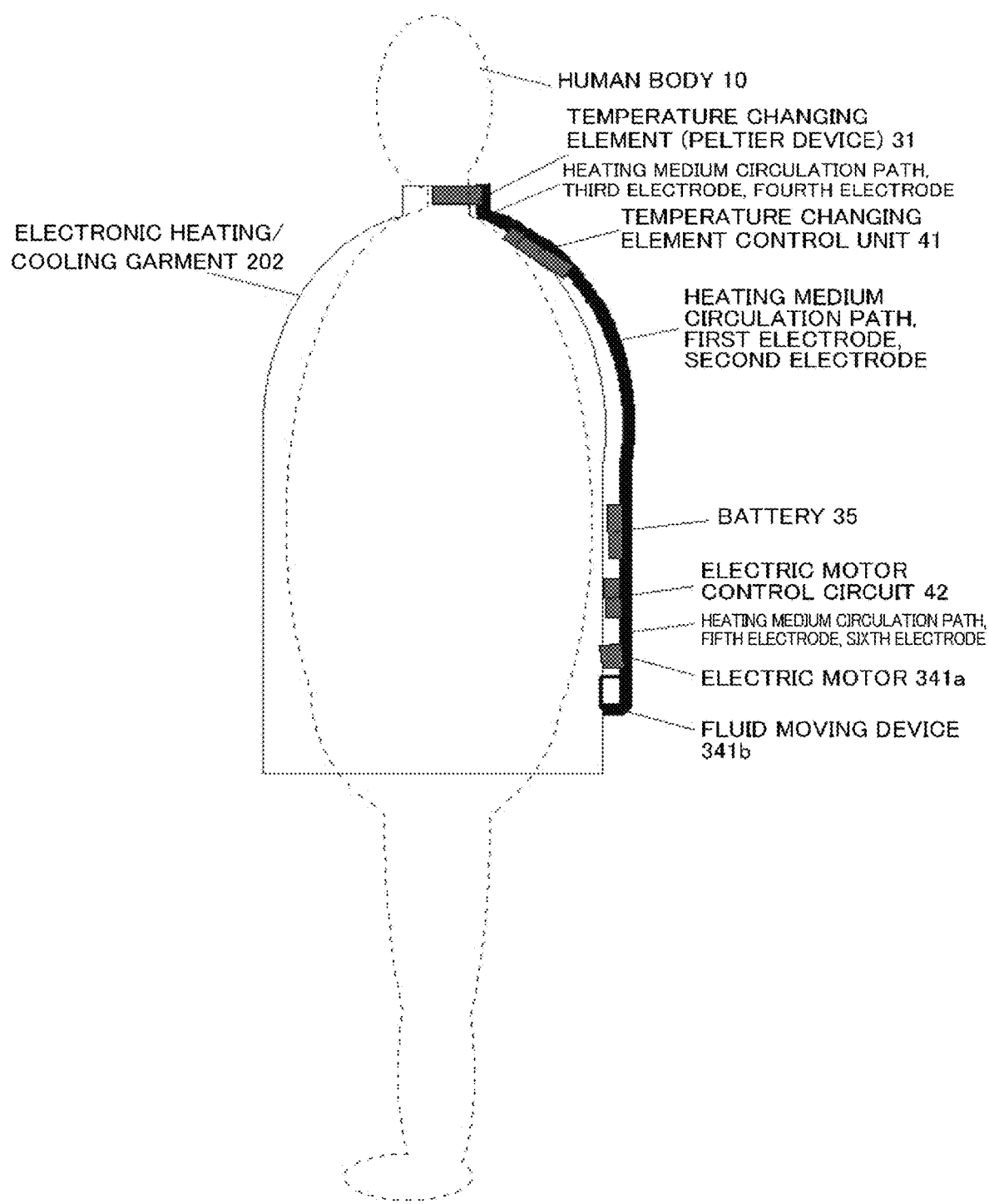
FIG. 7 is a longitudinal section of another electronic heating/cooling garment of the second example of the first embodiment.

FIG. 7 is a longitudinal section of another electronic heating/cooling garment 202 of the second example of the first embodiment. The Peltier device 31, a part of the heating medium circulation path 34 which is located immediately below the Peltier device 31, and parts of the third and fourth electrodes 433, 444 are placed inside the electronic heating/cooling garment 202. All other components are placed outside the electronic heating/cooling garment 202. In this case, heat is hardly transferred between the heating medium circulation path 34 and the inside of the electronic heating/cooling garment 202. Most of the heat is transferred between the heating medium circulation path 34 and the external environment. The electronic heating/cooling garment 202 has an opening though which the heating medium circulation path 34 passes so that the heating medium circulation path 34 is located inside and outside the electronic heating/cooling garment 202.

Although not shown in the figures, instead of the electrode also functioning as the heat absorption/dissipation fins as shown in FIG. 4, the heating medium circulation path 34 may be provided with well-known dedicated fins exclusively for heat dissipation or heat absorption. In this case, it is desirable to place the heat dissipation fins in the lower part of the front or back body.

Example of Second Embodiment

Figure 8:
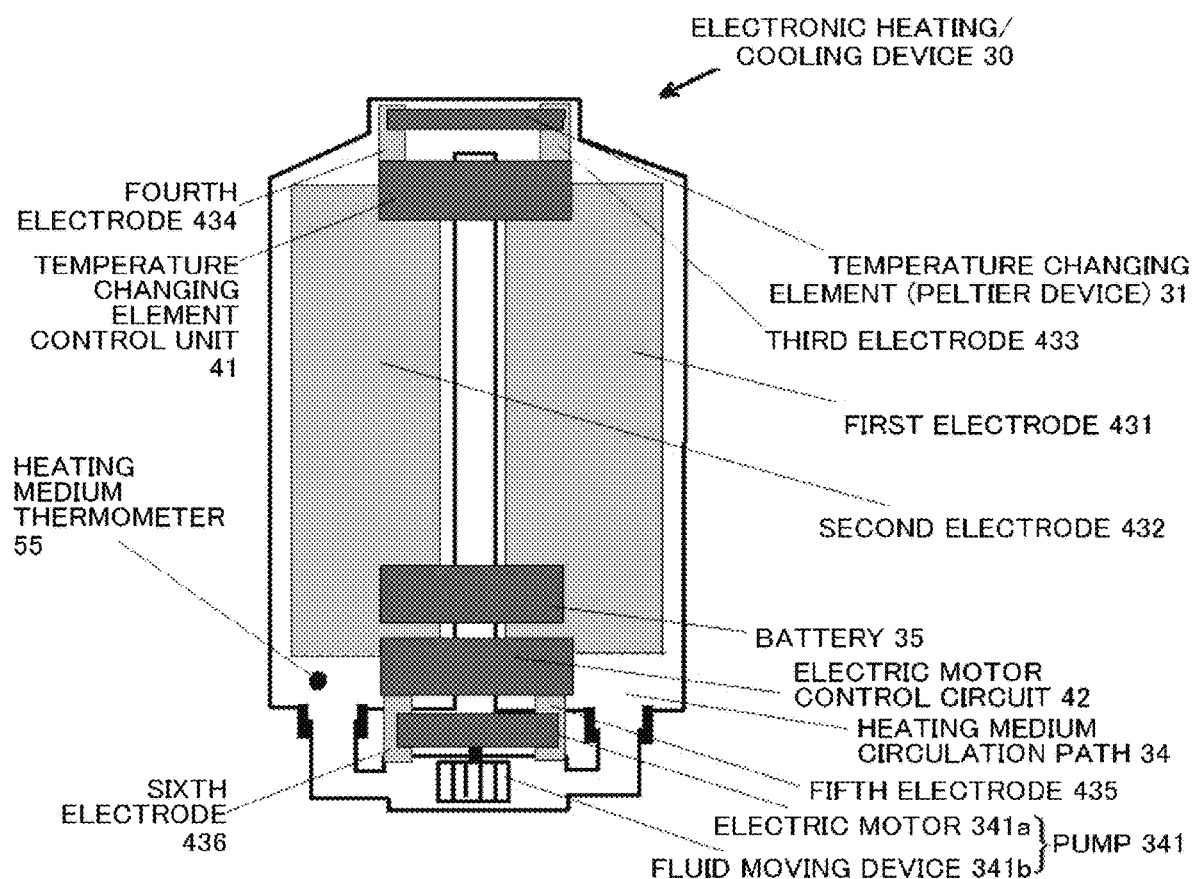
FIG. 8 illustrates an example of an electronic heating/cooling device according to an example of a second embodiment.

FIG. 8 illustrates an example of an electronic heating/cooling device 30 according to an example of a second embodiment. In FIG. 8, there is no garment shown by long dashed short dashed line in FIG. 2. However, since the configurations and functions of the components are similar to the second example of the first embodiment, these components are denoted with the same reference characters, and description thereof will be omitted. A hook of a hook-and-loop fastener is attached to the surface of the heating medium circulation path 34 of the electronic heating/cooling device 30 which faces a garment (the surface on the back side of the paper of FIG. 2). Accordingly, the heating medium circulation path 34 can be easily fastened to the inner surface of any garment which has a loop of the hook-and-loop fastener attached thereto. That is, in the case where the fastening method shown in FIG. 6 is used, the electronic heating/cooling device 30 can be fastened to any commercially available garment as long as the inner surface (the surface facing the human body) of the garment has a loop thereon. A well-known fastener (a hook and eye fastener or a snap) may be used to attach and detach the electronic heating/cooling device 30 to and from the garment.

By owning only one electronic heating/cooling device 30, the user can turn any ordinary clothes into an electronic heating/cooling garment. The electronic heating/cooling device 30 can also be easily detached (removed) from the electronic heating/cooling garment so that the garment can be worn as ordinary clothes. The electronic heating/cooling device 30 detached (removed) from the garment can be attached to other clothes. The sensors such as various vital sensors may be placed as appropriate in the electronic heating/cooling device 30 or may be attached to the garment such that the sensors come in contact with various parts of the human body.

Other Example 1

Although the electronic technology has remarkably advanced in recent years, every component of the electronic heating/cooling device is improved at a different pace regarding performance, efficiency, power saving, size reduction, cost reduction, etc. It is therefore desired to provide a technique for upgrading the electronic heating/cooling device by replacing a part of the components rather than by replacing the entire electronic heating/cooling device. That is, it is a third object of the present invention to provide a technique that makes it possible to replace a part of the components of the electronic heating/cooling garment or a part of the components of the electronic heating/cooling device that is attachable to and detachable from a garment.

The above third object can be achieved by the following means. In the first and second embodiments, a part of the sensors is directly attached to the garment, but the other members are fastened to the heating medium circulation path 34. The members that are fastened to the heating medium circulation path 34 are the temperature changing element (Peltier device) 31, the temperature changing element control unit 41, the battery 35, the electric motor control circuit 42, the electric motor 341*a*, the electric motor 342*a*, the fluid moving device 341*b*, and the fluid moving device 342*b*. The members that are directly fastened to the heating medium circulation path 34 are the fluid moving device 341*b* and the fluid moving device 342*b*, and the other members are fastened to two or more of the electrodes. Although the heating medium thermometer 55 is placed near the heating medium circulation path 34, the heating medium thermometer 55 is not fastened to the electrodes, operates on an internal battery, and wirelessly sends and receives information. It is therefore easy to replace the heating medium thermometer 55.

The fluid moving device 341*b* and the fluid moving device 342*b* can be replaced by a well-known method similar to a method used to replace a common mechanical member pressure-bonded to a main body without using an adhesive or pressure-fixed to the main body by screwing when the mechanical member is broken. That is, the fluid moving device 341*b* and the fluid moving device 342*b* pressure-inserted in the main body of the heating medium circulation path 34 so that the heating medium does not leak can be removed from the main body and replaced with new ones.

In a well-known method for replacing an electronic component fastened to electrodes, the electronic component is unscrewed and replaced. However, this method cannot be used because all of the first to sixth electrodes 431 to 436 that are required to be flexible are made of thin foil. Accordingly, replacement is performed by the following non-conventional method.

Among the members fastened to the electrodes, the temperature changing element (Peltier device) 31 is fastened to the third electrode 433 and the fourth electrode 434. The temperature changing element control unit 41 is fastened to the first electrode 431, the second electrode 432, the third electrode 433, and the fourth electrode 434. The battery 35 is fastened to the first electrode 431 and the second electrode 432. The electric motor control circuit 42 is fastened to the first electrode 431, the second electrode 432, the fifth electrode 435, and the sixth electrode 436. The electric motor 341*a* and the electric motor 342*a* are fastened to the fifth electrode 435 and the sixth electrode 436.

Each of the input and output terminals of the above electronic member should be located within a predetermined region. That is, each terminal should be located on the electrode to which the terminal should be connected. When these conditions are satisfied, the electronic members can be easily replaced as follows.

The surfaces of the first electrode 431 to the sixth electrode 436 on which the electronic components are placed are the loops of hook-and-loop fasteners. This is in order to prevent the first to sixth electrodes 431 to 436 from unnecessarily sticking to the garment or picking up lint. In order for the first to sixth electrodes 431 to 436 to function as electrodes, the loops are electrically conductive.

The input and output terminals of the electronic components are hooks. In order for the input and output terminals to function as electrodes, the hooks are electrically conductive. That is, the input and output terminals of the temperature changing element (Peltier device) 31, the temperature changing element control unit 41, the battery 35, the electric motor control circuit 42, the electric motor 341*a*, and the electric motor 342*a* are electrically conductive hooks.

The electrodes can thus be fastened to the electronic components by pressing each electrode and each electronic component together with a slightly strong force. Once fastened, the electrode and the electronic component are not separated from each other with a normal force. Each electrode and each electronic component are pulled apart with a slightly strong force when separating the electrode from the electronic component.

Another fastening method is to press the heating medium circulation path 34 having electrodes with the garment and the electronic components. However, the portion to be pressed is a part of the heating medium circulation path 34, and is pressed so as not to significantly hinder the flow of the heating medium. Specifically, the input and output terminals of the temperature changing element (Peltier device) 31, the temperature changing element control unit 41, the battery 35, the electric motor control circuit 42, the electric motor 341*a*, and the electric motor 342*a* and the electrodes of the heating medium circulation path 34 are fastened to a garment with a loop by using a band with a hook. This method is advantageous in that the terminals of the electronic components need not have a special shape.

Other Example 2

Figure 10:
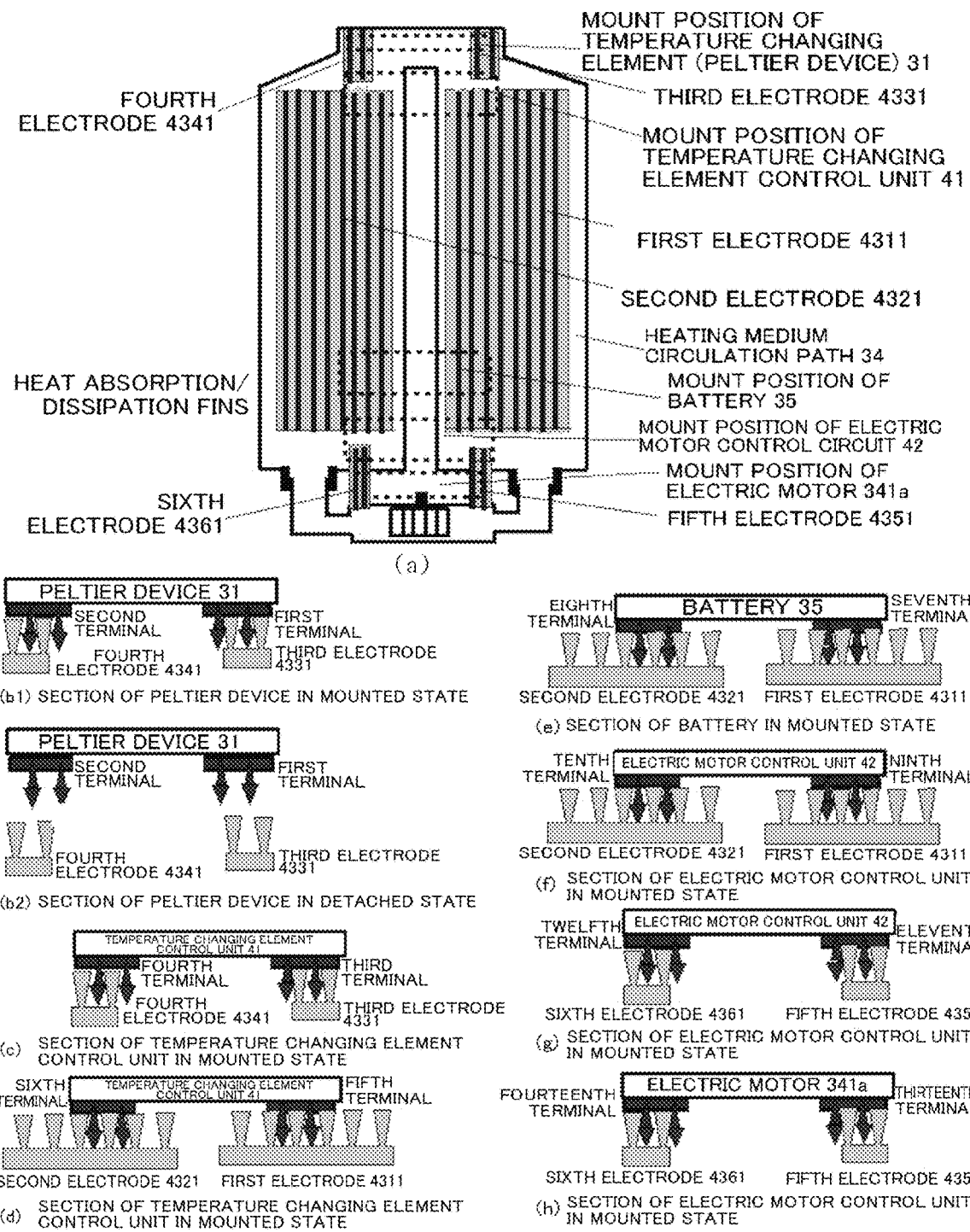
FIG. 10 illustrates a modification of the electrodes placed on the outer surface of the heating medium circulation path of the first and second embodiments.

FIG. 10 illustrates a modification of the electrodes placed on the outer surface of the heating medium circulation path. The electrodes shown in FIG. 10 function as both heat absorption/dissipation fins and hook-and-loop fasteners. FIG. 10(*a*) is a plan view of a first electrode 4311, a second electrode 4321, a third electrode 4331, a fourth electrode 4341, a fifth electrode 4351, and a sixth electrode 4361 which are placed on the outer surface of the heating medium circulation path 34. The rectangular areas shown by dashed lines in FIG. 10(*a*) indicate the places where the temperature changing element (Peltier device) 31, the temperature changing element control unit 41, the battery 35, and the electric motor 341*a* are placed.

FIGS. 10(*d*), 10(*e*), and 10(*f*) are partial sectional views of the first electrode 4311 and the second electrode 4321. FIGS. 10(*b*1), 10(*b*2), and 10(*c*) are sectional views of the third electrode 4331 and the fourth electrode 4341. FIGS. 10(*g*) and 10(*h*) are sectional views of the fifth electrode 4351 and the sixth electrode 4361.

As shown in FIG. 10(*a*), the heat absorption/dissipation fins of the first to sixth electrodes 4311 to 4361 have a linear planar shape. As shown in FIGS. 10(*b*1) to 10(*h*), each of the heat absorption/dissipation fins of the first to sixth electrodes 4311 to 4361 has a tapered sectional shape that becomes gradually thinner toward the heating medium circulation path 34 and becomes gradually wider toward the electronic component. Each heat absorption/dissipation fin has a spring force and bends in a direction perpendicular to the direction in which the heat absorption/dissipation fin extends linearly. That is, each electrode has linear fins arranged next to each other and parallel to its surface, and each fin has a sectional shape that becomes gradually thinner toward the heating medium circulation path, and has a spring force in the direction perpendicular to the direction in which the fin extends linearly.

As shown in FIG. 10(b2), when the Peltier device 31 is in the detached state, first and second terminals of the Peltier device 31 are not connected to the first third electrode 4331 and the fourth electrode 4341. Although not shown in the figures, the detached states of the temperature changing element control unit 41, the battery 35, the electric motor control circuit 42, and the electric motor 341a are similar to FIG. 10(b2).

The first terminal and the second terminal are terminals that supply electric power to the Peltier device 31. A third terminal and a fourth terminal shown in FIG. 10(c) are terminals on the output side of the temperature changing element control unit 41. A fifth terminal and a sixth terminal shown in FIG. 10(d) are terminals on the input side of the temperature changing element control unit 41. A seventh terminal and an eighth terminal shown in FIG. 10(e) are positive and negative terminals of the battery 35. A ninth terminal and a tenth terminal shown in FIG. 10(f) are terminals on the input side of the electric motor control circuit 42. An eleventh terminal and a twelfth terminal shown in FIG. 10(g) are terminals on the output side of the electric motor control circuit 42. A thirteenth terminal and a fourteenth terminal shown in FIG. 10(h) are terminals of the electric motor 341a.

As shown in FIGS. 10(b1) and 10(c) to FIG. 10(h), each of the first to fourteenth terminals that are the terminals of the electronic components is inserted between adjacent ones of the heat absorption/dissipation fins and is pressure-fitted in one of the first to sixth electrodes 4311 to 4361 by the spring force so that a current flows therebetween. When the terminals are in this pressure-fitted state, each electronic component is in its mounted state.

FIGS. 10(c) and 10(d) illustrates the temperature changing element control unit 41 in the mounted state. FIG. 10(e) illustrates the battery 35 in the mounted state. FIGS. 10(f) and 10(g) illustrate the electric motor control circuit 42 in the mounted state. FIG. 10(h) illustrates the electric motor 341a in the mounted state.

Like the hook-and-loop fasteners having a loop and a hook, each electronic component that is too thin to use a bolt and a nut can be attached and detached to the electrode by using such heat absorption/dissipation fins and the terminals fitted in the fins. The electronic component and the electrode are pressed against each other when mounting the electronic component on the electrode, and are pulled apart when detaching (removing) the electronic component from the electrode.

Other Example 3

The first and second embodiments are described with reference to the figures with respect to the case where the body part to be heated and cooled by the Peltier device is near a large blood vessel running through the neck. However, as described above, the part of the human body which should be heated and cooled in order to properly maintain the deep body temperature is not limited to the neck. The parts of the human bodies where those blood vessels which circulate blood throughout the body to keep important organs such as the brain and heart working run near the skin include not only the neck but also the armpit. Accordingly, heating and cooling the armpit instead of the neck has an effect similar to that of heating and cooling the neck. Heating and cooling both the neck and the armpit also has a similar effect. In the case where the garment is underwear, the Peltier device is fastened to a part of the underwear which comes in contact with the armpit of the human body. The armpit can thus be heated and cooled.

Other Example 4

A heating medium circulation path having electrodes so that the Peltier device can be mounted on any of the portions corresponding to the neck part, the collar (neckband), and the underarm part may be manufactured, and the Peltier device may be placed only in a desired place (e.g., only in the neck part). The electrodes and the heating medium circulation path are made of flexible materials. Accordingly, in the case where the electrodes and the heating circulation path are made longer, the electrodes and the heating circulation path can be attached to various clothes of different sizes from underwear to coat by slackening the electrodes and the heating circulation path. Moreover, variations in height and weight of wearers can be adjusted by the amount by which the electrodes and the heating circulation path are slackened.

Other Example 5

As shown in FIG. 3, the temperature changing element control unit 41 may be able to send and receive information to and from a server 70, a contract medical institution 80, and a contract security company 90 via the Internet. For example, the server 70 provides the latest programs that are executed by the arithmetic unit 411 of the temperature changing element control unit 41 and general information such as news to the wearer. For example, the contract medical institution 80 receives the wearer's vital signs to manage his or her health conditions. If there is a problem with any of the vital signs, the contract medical institution 80 contacts the wearer and gives appropriate instructions as determined by artificial intelligence (AI) of the server or a physician who belongs to the contract medical institution 80. For example, the contract security company 90 obtains the position of the wearer by a Global Positioning System (GPS) in the temperature changing element control unit 41 in order to prevent wandering of the old wearer from wandering about. In case of emergency, the contract security company 90 sends someone to inform the wearer of local information such as tsunami warning.

A wearer's smartphone may be used to send or receive information to and from the server and the external organizations via the Internet. Alternatively, a display, a speaker, earphones, a microphone, etc. mounted on the temperature changing element control unit 41, which are not shown in FIG. 3, may be used. If communication between the temperature changing element control unit 41 and the outside via the Internet is lost (e.g., when the wearer is isolated to a place with no signal reception due to a disaster), the temperature changing element control unit 41 detects the disconnection from the Internet. According to processing instructions stored in an internal memory of the arithmetic unit 411, the temperature changing element control unit 41 then causes the electronic heating/cooling device 30 or the electronic heating/cooling garment 202 to function as a standalone device that operates independently without using information from the outside. The electronic heating/cooling device 30 or the electronic heating/cooling garment 202 thus functions as a life support function even in harsh environments such as disaster areas.

The present invention is not limited to the above embodiments, and new embodiments and examples can be implemented by combining all or a part of the configurations of the embodiments and examples illustrated in the specification and the drawings.

DESCRIPTION OF REFERENCE CHARACTERS

10 Human Body
20 Electronic Heating/Cooling Garment
30 Electronic Heating/Cooling Device
31 Temperature Changing Element (Peltier device)
32 First Electrode
33 Second Electrode
34 Heating Medium Circulation Path
35 Battery
41 Temperature Changing Element Control Unit
42 Electric Motor Control Circuit
54 Ambient Air Thermometer
55 Heating Medium Thermometer
70 Server
80 Contract Medical Institution
90 Contract Security Company
201 Electronic Heating/Cooling Garment
202 Electronic Heating/Cooling Garment
341 Pump
341*a* Electric Motor
341*b* Fluid Moving Device
342 Pump
342*a* Electric Motor
342*b* Fluid Moving Device
411 Arithmetic Unit
412 Peltier device Power Controller
421 Electric Motor Power Controller
431 First Electrode
432 Second Electrode
433 Third Electrode
434 Fourth Electrode
435 Fifth Electrode
4311 First Electrode
4321 Second Electrode
4331 Third Electrode
4341 Fourth Electrode
4351 Fifth Electrode
4361 Sixth Electrode

The invention claimed is:

1. An electronic heating/cooling device, comprising:
a temperature changing element that is configured to come in contact with skin covering a large blood vessel;
a heating medium circulation path thermally coupled to an opposite surface of the temperature changing element from a surface that is configured to come in contact with the skin;
a pump that is a part of the heating medium circulation path and is configured to circulate a heating medium; and
a battery configured to supply electric power to the pump and the temperature changing element, wherein
the heating medium circulation path is composed of a flexible, thermally conductive material having a tubular shape, holds the circulating heating medium in a tubular internal space in an airtight manner, and has a first electrode and a second electrode, the first and second electrodes being made of a flexible, electrically conductive material and being configured to supply the electric power from the battery to the temperature changing element and the pump,
the heating medium circulation path is made of a non-electrically conductive material,
the first electrode is a first flexible, electrically conductive foil material attached to an outer surface of the heating medium circulation path, and
the second electrode is a second flexible, electrically conductive foil material attached to the outer surface of the heating medium circulation path.

2. The electronic heating/cooling device of claim 1, further comprising:
fins in the shape of protrusions extending parallel to a surface of the first flexible, electrically conductive foil material and a surface of the second flexible, electrically conductive foil material, wherein
the fins have a sectional shape that becomes gradually thinner toward the heating medium circulation path, and
the fins have a spring three in a direction perpendicular to a direction in which the fin extends.

3. An electronic heating/cooling device, comprising:
a temperature changing element that is configured to come in contact with skin covering a large blood vessel;
a heating medium circulation path thermally coupled to an opposite surface of the temperature changing element from a surface that is configured to come in contact with the skin;
a pump that is a part of the heating medium circulation path and is configured to circulate a heating medium; and
a battery configured to supply electric power to the pump and the temperature changing element, wherein
the heating medium circulation path is composed of a flexible, thermally conductive material having a tubular shape, holds the circulating heating medium in a tubular internal space in an airtight manner, and has a first electrode and a second electrode, the first and second electrodes being made of a flexible, electrically conductive material and being configured to supply the electric power from the battery to the temperature changing element and the pump,
the heating medium circulation path has a flexible, electrically conductive material portion made of a flexible, electrically conductive material, and a flexible, non-electrically conductive material portion made of a flexible, non-electrically conductive material,
the first electrode is a first flexible, electrically conductive material portion,
the second electrode is a second flexible, electrically conductive material portion,
a first flexible, non-electrically conductive portion is coupled between one end of the first flexible, electrically conductive material portion and one end of the second flexible, electrically conductive material portion, and
a second flexible, non-electrically conductive material is coupled between the other end of the first flexible, electrically conductive material portion and the other end of the second flexible, electrically conductive material portion.

4. An electronic heating cooling device, comprising:
a temperature changing element that is configured to come in contact with skin covering a large blood vessel;

a heating medium circulation path thermally coupled to an opposite surface of the temperature changing element from a surface that is configured to come in contact with the skin;
a pump that is a part of the heating medium circulation path and is configured to circulate a heating medium; and
a battery configured to supply electric power to the pump and the temperature changing element, wherein
the heating medium circulation path is composed of a flexible, thermally conductive material having a tubular shape, holds the circulating heating medium in a tubular internal space in an airtight manner, and has a first electrode and a second electrode, the first and second electrodes being made of a flexible, electrically conductive material and being configured to supply the electric power from the battery to the temperature changing element and the pump,
the heating medium circulation path is made of a non-electrically conductive material,
the first electrode is a first plating portion or a first electrically conductive paint portion on an outer surface of the heating medium circulation path, and
the second electrode is a second plating portion or a second electrically conductive paint portion on the outer surface of the heating medium circulation path.

* * * * *